US012583867B2

(12) United States Patent
Shao et al.

(10) Patent No.: US 12,583,867 B2
(45) Date of Patent: Mar. 24, 2026

(54) PYRIDONE DERIVATIVE CRYSTAL FORM AND PREPARATION METHOD AND APPLICATION THEREFOR

(71) Applicant: Jiangxi Caishi Pharmaceutical Technology Co., Ltd., Jiangxi (CN)

(72) Inventors: Qing Shao, Suzhou (CN); Libin Gan, Suzhou (CN); Li Chen, Suzhou (CN)

(73) Assignee: Jiangxi Caishi Pharmaceutical Technology Co., Ltd., Jiangxi (CN)

( * ) Notice: Subject to any disclaimer, the term of this patent is extended or adjusted under 35 U.S.C. 154(b) by 1061 days.

(21) Appl. No.: 17/595,013

(22) PCT Filed: Nov. 5, 2019

(86) PCT No.: PCT/CN2019/115641

§ 371 (c)(1),
(2) Date: Apr. 27, 2022

(87) PCT Pub. No.: WO2020/224208

PCT Pub. Date: Nov. 12, 2020

(65) Prior Publication Data

US 2023/0144122 A1 May 11, 2023

(30) Foreign Application Priority Data

May 8, 2019 (CN) ......................... 201910381020.0

(51) Int. Cl.

| | |
|---|---|
| ***C07D 498/14*** | (2006.01) |
| ***A61K 31/5383*** | (2006.01) |
| ***A61K 31/55*** | (2006.01) |
| ***A61P 31/16*** | (2006.01) |

(52) U.S. Cl.

CPC ........ *C07D 498/14* (2013.01); *A61K 31/5383* (2013.01); *A61K 31/55* (2013.01); *A61P 31/16* (2018.01); *C07B 2200/13* (2013.01)

(58) Field of Classification Search

CPC ................ C07D 498/14; C07D 498/20; C07B 2200/13; A61K 31/5383; A61K 31/55; A61P 31/16

See application file for complete search history.

(56) References Cited

U.S. PATENT DOCUMENTS

| | | | |
|---|---|---|---|
| 8,927,710 B2 | 1/2015 | Akiyama et al. | |
| 8,987,441 B2 | 3/2015 | Takahashi et al. | |
| 9,469,638 B2 | 10/2016 | Akiyama et al. | |
| 9,815,835 B2 | 11/2017 | Akiyama et al. | |
| 10,160,764 B2 | 12/2018 | Jain et al. | |
| 11,247,993 B2 * | 2/2022 | Chen | C07D 471/14 |
| 2016/0228438 A1 | 8/2016 | Hendricks et al. | |

(Continued)

FOREIGN PATENT DOCUMENTS

| | | | |
|---|---|---|---|
| AU | 2017310774 A1 | 2/2018 |
| CN | 102803260 A | 11/2012 |

(Continued)

OTHER PUBLICATIONS

Florence, A.J. "Polymorph Screening in Pharmaceutical Development." European Pharmaceutical Review. Aug. 2010. https://www.europeanpharmaceuticalreview.com/article/3659/polymorph-screening-in-pharmaceutical-development/. Accessed Jul. 22, 2025. (Year: 2010).*

(Continued)

*Primary Examiner* — Clinton A Brooks
*Assistant Examiner* — Kyle Nottingham
(74) *Attorney, Agent, or Firm* — Knobbe, Martens, Olson & Bear, LLP

(57) ABSTRACT

Crystals of (((R)-12'-((S)-7,8-difluoro-6,11-dihydrodibenzo[b,e]thiepin-11-yl)-6',8'-dioxo-6',8',12',12a'-tetrahydro-1'H,4'H-spiro[cyclopropane-1,3'-[1,4]oxazino[3,4-c]pyrido[2,1-f][1,2,4]triazin]-7'-yl)oxy)methyl methyl carbonate, i.e. compound of formula (1) or a solvate thereof and a preparation method therefor. The crystals include crystal form A, crystal form B, crystal form C, crystal form D, crystal form E, crystal form F, and single crystal. The crystal of the compound of formula (1) or a solvate thereof can be individually used for clinical treatment or in combination with other anti-influenza drugs such as neuraminidase inhibitors, nucleoside drugs, or PB2 inhibitors, are capable of clinically curing influenza patients quickly, and have very good activity and good bioavailability compared to existing pyridone derivatives. In addition, the stability, hygroscopicity, and storability of the crystals meet the requirements for pharmaceutical use.

(1)

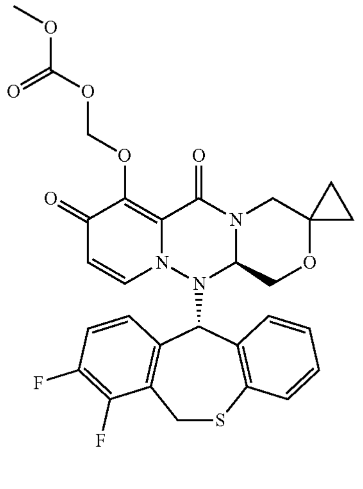

33 Claims, 10 Drawing Sheets

(56) References Cited

U.S. PATENT DOCUMENTS

| | | | | |
|---|---|---|---|---|
| 2018/0118760 | A1* | 5/2018 | Kawai | A61K 9/0014 |
| 2019/0367517 | A1* | 12/2019 | Chen | C07D 471/04 |

FOREIGN PATENT DOCUMENTS

| | | | |
|---|---|---|---|
| CN | 103228653 | A | 7/2013 |
| CN | 108697715 | A | 10/2018 |
| CN | 109721615 | A | 5/2019 |
| CN | 110041327 | A | 7/2019 |
| EP | 2444400 | A1 | 4/2012 |
| EP | 2620436 | A1 | 7/2013 |
| EP | 3290424 | A1 | 3/2018 |
| EP | 3498281 | A1 | 6/2019 |
| IN | 202047035079 | A | 9/2020 |
| JP | 5971830 | B1 | 8/2016 |
| JP | 2017-137291 | A | 8/2017 |
| JP | 6249434 | B1 | 12/2017 |
| SG | 174598 | A1 | 10/2011 |
| SG | 11201708721 XA | | 11/2017 |
| WO | WO 2010/147068 | A1 | 12/2010 |
| WO | WO 2012/039414 | A1 | 3/2012 |
| WO | WO 2016/094198 | A1 | 6/2016 |
| WO | WO 2016/175224 | A1 | 11/2016 |
| WO | WO 2017/104691 | A1 | 6/2017 |
| WO | WO 2017/153919 | A1 | 9/2017 |
| WO | WO 2018/030463 | A1 | 2/2018 |
| WO | WO 2018/042303 | A1 | 3/2018 |
| WO | WO 2019/141179 | A1 | 7/2019 |

OTHER PUBLICATIONS

International Search Report issued in International Application No. PCT/CN2019/115641, mailed on Feb. 3, 2020.

Banker et al., "Modern Pharmaceutics." Prodrugs, Third Edition, 1996, pp. 451 and 596.

Bundgaard, H., "Design of prodrugs: Bioreversible derivatives for various functional groups and chemical entities." Design of Prodrugs, Elsevier, 1985, in 3 pages.

Griffiths, P.D., "Cytomegalovirus." Principles and Practice of Clinical Virology, Fifth Edition, John Wiley & Sons Ltd., 2004, pp. 85-122.

Müller et al., "Antiviral Strategies." Handbook of Experimental Pharmacology, 2009, 189: 1-24.

Poupaert et al., "Drug Design: Basic Principles and Applications." Encyclopedia of Pharmaceutical Technology, 2017, pp. 1362-1369.

Sharpless et al., "The mighty mouse: genetically engineered mouse models in cancer drug development." Nature Reviews Drug Discovery, 2006, pp. 1-14.

Silverman, R.B., "Prodrugs and Drug Delivery Systems." The Organic Chemistry of Drug Design and Drug Action, Academic Press, Inc., 1992, pp. 352-400.

Sun et al., "Synthesis and evaluation of a new series of substituted acyl(thio)urea and thiadiazolo [2,3,-α] pyrimidine derivatives as potent inhibitors of influenza virus neuraminidase." Bioorganic & Medicinal Chemistry, 2006, 14: 8574-8581.

Ulrich et al., "Crystallization." Kirk-Othmer Encyclopedia of Chemical Technology, 2002, pp. 1-7.

Vippagunta et al., "Crystalline solids." Advanced Drug Delivery Reviews, 2001, 48: 3-26.

Wolff, M.E., "Burger's Medicinal Chemistry and Drug Discovery, vol. I: Principles and Practice." John Wiley & Sons, 1995, pp. 975-977.

Zon et al., "In Vivo Drug Discovery in the Zebrafish." Nature Reviews Drug Discovery, 2005, 4:35-44.

* cited by examiner

PYRIDONE DERIVATIVE CRYSTAL FORM AND PREPARATION METHOD AND APPLICATION THEREFOR

TECHNICAL FIELD

The present application belongs to the field of medicinal chemistry, and specifically relates to crystal forms of a pyridone derivative with an influenza virus inhibitory effect, and a preparation method and use thereof.

BACKGROUND

Influenza viruses are highly contagious and easily cause acute respiratory infections, which affects 5%-20% of adults and 20%-30% of children every year. In special groups, such as those over 65 years of age or those suffering from chronic underlying diseases, influenza viruses can easily cause severe respiratory or cardiovascular complications, and have caused hundreds of thousands of deaths worldwide each year.

Neuraminidase inhibitors Oseltamivir and Zanamivir can inhibit the spread of the viruses, but must be taken within 48 hours after infection. In addition, influenza viruses are prone to antigenic variation, for example, the Spanish influenza in 1918 was caused by the H1N1 subtype, the Asian influenza in 1957 was caused by the H2N2 subtype, the Hong Kong influenza in 1968 was caused by the H3N2 subtype, and the influenza from 2007 to 2008 was caused by the H5N1 subtype. Concerning the new influenza virus pandemic and the development of drug resistance of existing drugs, there is an urgent clinical need for anti-influenza drugs with a new mechanism.

Influenza viruses are RNA viruses, and their genetic material is single negative-strand RNA. The transcription and replication of antisense RNA of the viruses is an important step in the life course of the influenza viruses. RNA polymerase is composed of three subunits, PA, PB1 and PB2, which is responsible for the replication and transcription of viral RNA in the nuclei of infected host cells. The transcription of influenza virus RNA has a special “cap snatching” mechanism, the PB2 subunit is responsible for recognizing and binding to the “cap structure” of the mRNA precursors of host cell, and the PA subunit is responsible for editing the mRNA precursors of host cell, forming primers to initiate the transcription process. PB1 subunit is responsible for the synthesis of virus mRNA. Wherein, the cap-dependent endonuclease action of the PA subunit is necessary for the life process of the viruses, and has specificity that the host cell does not possess, and is suitable as a brand-new target for developing new anti-influenza drugs.

In addition, the crystal structures of the active pharmaceutical ingredients often cause differences in various physical and chemical properties of the drugs, such as solubility, dissolution rate, melting point, density, hardness, etc., which directly affect the prescription preparation processes, storage methods, and pharmacokinetics in vivo of the drug, and then affect the bioavailability, clinical efficacy and safety of the drugs. Therefore, it is very important to study the polymorphism of drugs in depth and to find crystal forms with good properties.

SUMMARY

The problem to be solved by this application is to provide a novel pyridone derivative which has high bioavailability and can be transformed into a compound with strong inhibitory activity against influenza A virus and influenza B virus after being taken by the human body.

Meanwhile, the present application further provides a plurality of crystals of the novel pyridone derivative or a solvate thereof, and the stability, hygroscopicity, and solubility of the crystals meet the requirements for pharmaceutical use.

Meanwhile, the present application further provides preparation methods of the above-mentioned crystals and their use in the preparation of anti-influenza virus drugs.

To solve the above-mentioned problems, one aspect of the present application provides a crystal of a compound of formula (1) or a solvate thereof:

Formula (1)

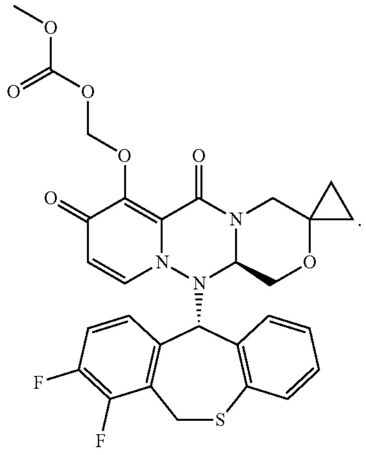

The Chinese name of the compound of formula (1) is: (((R)-12'-((S)-7,8-二氟-6,11-二氢二苯并[b,e]噻庚英-11-基)-6',8'-二氧代-6',8',12',12a'四氢-1'H-,4'H-螺[环丙烷-1,3'-[1,4]恶嗪并[3,4-c]吡啶并[2,1-f][1,2,4]三嗪]-7'-基)氧基)甲基碳酸甲酯;

The English name of the compound of formula (1) is: (((R)-12'-((S)-7,8-difluoro-6,11-dihydrodibenzo[b,e]thiepin-11-yl)-6',8'-dioxo-6',8',12',12a'-tetrahydro-1'H,4'H-spiro[cyclopropane-1,3'-[1,4]oxazino[3,4-c]pyrido[2,1-f][1,2,4]triazin]-7'-yl)oxy)methyl methyl carbonate.

According to some preferred aspects of the present application, the present application provides a crystal form A of the compound of formula (1), which has an X-ray powder diffraction pattern (the radiation source used is Cu-Kα, the same below) with characteristic peaks at 2θ of 3.10°±0.2°, 8.74°±0.2°, 15.44°±0.2°, and 21.91°±0.2°. In some specific implementations, the X-ray powder diffraction pattern of the crystal form A of the compound of formula (1) may further have one or more characteristic peaks at 2θ of 13.08°±0.2°, 26.35°±0.2°, and 30.83°±0.2°.

According to some specific aspects of the present application, the X-ray powder diffraction pattern of the crystal form A of the compound of formula (1) has characteristic peaks at 2θ of 3.10°±0.2°, 8.74°±0.2°, 13.08°±0.2°, 15.44°±0.2°, 21.91°±0.2°, 26.35°±0.2°, and 30.83°±0.2°.

According to some specific aspects of the present application, an XRPD pattern of the crystal form A of the compound of formula (1) is the same as shown in FIG. 1.

According to some specific aspects of the present application, a spectrum of the crystal form A of the compound of formula (1) determined by thermogravimetric analysis shows that it starts to lose weight when heated to 26.8±2° C., and loses 1.8±0.2% in weight when heated to 150±2° C.

According to some specific aspects of the present application, a spectrum of the crystal form A of the compound of formula (1) determined by differential scanning calorimetry shows one endothermic peak, indicating that a melting point onset temperature of the crystal form A is 230.5±2° C., and there is an endothermic peak at 232±2° C.

According to a specific and preferred aspect of the present application, the crystal form A of the compound of formula (1) is an anhydrous crystal form.

According to some other preferred aspects of the present application, the present application provides a crystal form B of the compound of formula (1), which has an X-ray powder diffraction pattern with characteristic peaks at 2θ of 8.42°±0.2°, 14.27°±0.2°, 16.04°±0.2°, and 25.41°±0.2°. In some specific implementations, the X-ray powder diffraction pattern of the crystal form B of the compound of formula (1) may further have one or two characteristic peaks at 2θ of 10.75°±0.2°, and 16.87°±0.2°.

In some specific implementations, the X-ray powder diffraction pattern of the crystal form B of the compound of formula (1) further has one or more characteristic peaks at 2θ of 18.21°±0.2°, 18.78°±0.2°, 19.26°±0.2°, 19.60°±0.2°, 20.40°±0.2°, 21.39°±0.2°, 21.66°±0.2°, 23.38°±0.2°, 27.32°±0.2°, 29.17°±0.2°, and 34.08°±0.2°.

According to some specific aspects of the present application, the X-ray powder diffraction pattern of the crystal form B of the compound of formula (1) has characteristic peaks at 2θ of 8.42°±0.2°, 10.75°±0.2°, 14.27°±0.2°, 16.04°±0.2°, 16.87°±0.2°, 18.21°±0.2°, 18.78°±0.2°, 19.26°±0.2°, 19.60°±0.2°, 20.40°±0.2°, 21.39°±0.2°, 21.66°±0.2°, 23.38°±0.2°, 25.41°±0.2°, 27.32°±0.2°, 29.17°±0.2°, and 34.08°±0.2°.

According to some specific aspects of the present application, an XRPD pattern of the crystal form B of the compound of formula (1) is the same as shown in FIG. 4.

According to some specific aspects of the present application, a spectrum of the crystal form B of the compound of formula (1) determined by thermogravimetric analysis shows that it starts to lose weight when heated to 22.6±2° C., and loses 2.2±0.2% in weight when heated to 15°±2° C.

According to some specific aspects of the present application, a spectrum of the crystal form B of the compound of formula (1) determined by differential scanning calorimetry shows two endothermic peaks, onset temperatures of the two endothermic peaks are 208.5±2° C. and 233.8±2° C., respectively, and there are endothermic peaks at 213.5±2° C. and 235.1±2° C., respectively.

According to a specific and preferred aspect of the present application, the crystal form B of the compound of formula (1) is an anhydrous crystal form.

According to some preferred aspects of the present application, the present application provides a crystal form C of the compound of formula (1), which has an X-ray powder diffraction pattern with characteristic peaks at 2θ of 7.73°±0.2°, 17.13°±0.2°, 20.08°±0.2°, and 21.74°±0.2°. In some specific implementations, the X-ray powder diffraction pattern of the crystal form C of the compound of formula (1) further has one or more characteristic peaks at 2θ of 13.13°±0.2°, 13.65°±0.2°, 20.98°±0.2°, and 23.22°±0.2°.

In some specific implementations, the X-ray powder diffraction pattern of the crystal form C of the compound of formula (1) may further have one or more characteristic peaks at 2θ of 12.51°±0.2°, 14.76°±0.2°, 15.21°±0.2°, 18.39°±0.2°, and 24.13°±0.2°.

According to some specific aspects of the present application, the X-ray powder diffraction pattern of the crystal form C of the compound of formula (1) has characteristic peaks at 2θ of 7.73°±0.2°, 12.51°±0.2°, 13.13°±0.2°, 13.65°±0.2°, 14.76°±0.2°, 15.21°±0.2°, 17.13°±0.2°, 18.39°±0.2°, 20.08°±0.2°, 20.98°±0.2°, 21.74°±0.2°, 23.22°±0.2°, and 24.13°±0.2°.

According to some specific aspects of the present application, an XRPD pattern of the crystal form C of the compound of formula (1) is the same as shown in FIG. 7.

According to some specific aspects of the present application, a spectrum of the crystal form C of the compound of formula (1) determined by thermogravimetric analysis shows that it starts to lose weight when heated to 25.9±2° C., and loses 12.1±0.2% in weight when heated to 15°±2° C.

According to some specific aspects of the present application, a spectrum of the crystal form C of the compound of formula (1) determined by differential scanning calorimetry shows two endothermic peaks, onset temperatures of the two endothermic peaks are 86.8±2° C. and 233.9±2° C., respectively, and there are endothermic peaks at 94.9±2° C. and 234.8±2° C., respectively.

According to a specific aspect of the present application, the crystal form C of the compound of formula (1) is a tetrahydrofuran solvate of the compound of formula (1).

According to some preferred aspects of the present application, the present application provides a crystal form D of the compound of formula (1), which has an X-ray powder diffraction pattern with characteristic peaks at 2θ of 7.94°±0.2°, 22.16°±0.2°, and 28.03°±0.2°. In some specific implementations, the X-ray powder diffraction pattern of the crystal form D of the compound of formula (1) may further have one or more characteristic peaks at 2θ of 15.09°±0.2°, 15.50°±0.2°, 19.63°±0.2°, 23.56°±0.2°, and 25.86°±0.2°.

According to some specific aspects of the present application, the X-ray powder diffraction pattern of the crystal form D of the compound of formula (1) has characteristic peaks at 2θ of 7.94°±0.2°, 15.09°±0.2°, 15.50°±0.2°, 19.63°±0.2°, 22.16°±0.2°, 23.56°±0.2°, 25.86°±0.2°, and 28.03°±0.2°.

According to some specific aspects of the present application, an XRPD pattern of the crystal form D of the compound of formula (1) is the same as shown in FIG. 10.

According to some specific aspects of the present application, a spectrum of the crystal form D of the compound of formula (1) determined by thermogravimetric analysis shows that it starts to lose weight when heated to 23.5±2° C., and loses 7.5±0.2% in weight when heated to 15°±2° C.

According to some specific aspects of the present application, a spectrum of the crystal form D of the compound of formula (1) determined by differential scanning calorimetry shows two endothermic peaks, onset temperatures of the two endothermic peaks are 113.2±2° C. and 230.6±2° C., respectively, and there are endothermic peaks at 140.4±2° C. and 232.4±2° C., respectively.

According to a specific aspect of the present application, the crystal form D of the compound of formula (1) is a N-methyl-2-pyrrolidone solvate of the compound of formula (1).

According to some preferred aspects of the present application, the present application provides a crystal form E of the compound of formula (1), which has an X-ray powder diffraction pattern with characteristic peaks at 2θ of 8.01°±0.2°, 8.78°±0.2°, and 26.33°±0.2°.

In some specific implementations, the X-ray powder diffraction pattern of the crystal form E of the compound of formula (1) further has one or more characteristic peaks at 2θ of 4.44°±0.2°, 17.56°±0.2°, 21.95°±0.2°, and 22.25°±0.2°.

In some specific implementations, the X-ray powder diffraction pattern of the crystal form E of the compound of formula (1) further has one or more characteristic peaks at 2θ of 5.87°±0.2°, 19.64°±0.2°, 28.15°±0.2°, 29.07°±0.2°, and 30.86°±0.2°.

According to some specific aspects of the present application, the X-ray powder diffraction pattern of the crystal form E of the compound of formula (1) has characteristic peaks at 2θ of 4.44°±0.2°, 5.87°±0.2°, 8.01°±0.2°, 8.78°±0.2°, 17.56°±0.2°, 19.64°±0.2°, 21.95°±0.2°, 22.25°±0.2°, 26.33°±0.2°, 28.15°±0.2°, 29.07°±0.2°, and 30.86°±0.2°.

According to some specific aspects of the present application, an XRPD pattern of the crystal form E of the compound of formula (1) is the same as shown in FIG. 13.

According to some preferred aspects of the present application, the present application provides a crystal form F of the compound of formula (1), which has an X-ray powder diffraction pattern with characteristic peaks at 2θ of 5.77°±0.2°, 8.69°±0.2°, 17.48°±0.2°, and 22.84°±0.2°.

In some specific implementations, the X-ray powder diffraction pattern of the crystal form F of the compound of formula (1) further has one or two characteristic peaks at 2θ of 11.61°±0.2°, and 19.47°±0.2°.

In some specific implementations, the X-ray powder diffraction pattern of the crystal form F of the compound of formula (1) further has one or more characteristic peaks at 2θ of 11.98°±0.2°, 13.84°±0.2°, 14.30°±0.2°, 18.33°±0.2°, and 18.95°±0.2°.

According to some specific aspects of the present application, the X-ray powder diffraction pattern of the crystal form F of the compound of formula (1) has characteristic peaks at 2θ of 5.77°±0.2°, 8.69°±0.2°, 11.61°±0.2°, 11.98°±0.2°, 13.84°±0.2°, 14.30°±0.2°, 17.48°±0.2°, 18.33°±0.2°, 18.95°±0.2°, 19.47°±0.2°, and 22.84°±0.2°.

According to some specific aspects of the present application, an XRPD pattern of the crystal form F of the compound of formula (1) is the same as shown in FIG. 19 or FIG. 20.

According to some specific aspects of the present application, a spectrum of the crystal form F of the compound of formula (1) determined by differential scanning calorimetry shows one endothermic peak, indicating that an onset temperature of the endothermic peak is 231.1±2° C., and there is an endothermic peak at 234.5±2° C.

According to a specific and preferred aspect of the present application, the crystal form F of the compound of formula (1) is an anhydrous crystal form.

According to a specific aspect of the present application, the crystal form F of the compound of formula (1) has an X-ray diffraction pattern substantially the same as FIG. 14, FIG. 19, or FIG. 20.

According to some preferred aspects of the present application, the present application further provides a crystal of the compound of formula (1) with a single crystal form, which belongs to orthorhombic crystal system, with space group $P2_12_12_1$, and unit-cell parameters are: a=11.7±0.2 Å, b=19.6±0.2 Å, c=23.4±0.2 Å, α=90°±0.2°, β=90°±0.2°, γ=90°±0.2°.

According to some preferred aspects of the present application, the unit-cell parameters are: a=11.65-11.75 Å, b=19.50-19.60 Å, c=23.33-23.43 Å, α=89.9-90.1°, β=89.9-90.1°, γ=89.9-90.1°.

According to some specific and preferred aspects of the present application, the unit-cell parameters are: a=11.70-11.73 Å, b=19.54-19.58 Å, c=23.35-23.40 Å, α=89.95-90.05°, β=89.95-90.05°, γ=89.95-90.05°.

In a specific implementation, the unit-cell parameters are: a=11.7243 (3) Å, b=19.5693 (6) Å, c=23.3801 (7) Å, α=β=γ=90°.

According to a specific aspect of the present application, a unit cell of the single crystal contains 8 molecules.

According to some specific and preferred aspects of the present application, a volume of the unit cell of the single crystal is 5364.2±0.1 $Å^3$. According to a specific aspect of the present application, the volume of the unit cell of the single crystal is 5364.2 (3) $Å^3$.

According to some specific and preferred aspects of the present application, a calculated density of the single crystal is 1.48°±0.1 $g/cm^3$. According to a specific aspect of the present application, the calculated density of the single crystal is 1.480 $g/cm^3$.

According to some preferred aspects of the present application, a method for preparing the single crystal comprises: dissolving the compound of formula (1) in an alcohol solvent, filtering, volatilizing the solvent in a filtrate at room temperature to precipitate crystals, collecting resulting crystals by filtration, and drying at room temperature to obtain. According to some specific aspects of the present application, the alcohol solvent comprises methanol, ethanol, etc.

Meanwhile, the present application further provides a technical solution: the present application provides a method for preparing the above-mentioned crystal form A of the compound of formula (1), and the method comprises:

1) adding the compound of formula (1) to one of or a mixture of more of an ester solvent (for example, isopropyl acetate, ethyl acetate, etc.), an alcohol solvent (for example, methanol, ethanol, isopropanol, etc.), and a ketone solvent (for example, acetone, butanone, etc.) to dissolve, then mixing with a hydrocarbon solvent (for example, n-heptane, etc.), crystallizing, filtering, and drying to give the crystal form A of the compound of formula (1); or
2) adding the compound of formula (1) to a ketone solvent (for example, acetone, etc.), volatilizing the solvent at room temperature to obtain a solid, and drying the resulting solid to give the crystal form A of the compound of formula (1); or
3) adding the compound of formula (1) to an ether solvent (for example, methyl tert-butyl ether, etc.), stirring at room temperature, filtering to obtain a solid, and drying the resulting solid to give the crystal form A of the compound of formula (1); or
3) adding the compound of formula (1) to water, stirring at 45-55° C., filtering to obtain a solid, and drying the resulting solid to give the crystal form A of the compound of formula (1); or
4) adding the compound of formula (1) to a mixture solvent of a hydrocarbon solvent (for example, methylbenzene, etc.) and an ether solvent (for example, methyl tert-butyl ether, etc.), stirring at a set temperature for 1 to 3 h, then heating up or cooling at a rate of 0.1±0.05° C./min to circulate the temperature of the system between the set temperature and 5° C. for several times, and finally stirring at 3-7° C., filtering to obtain a solid, and drying the resulting solid to give the crystal form A of the compound of formula (1), the set temperature is 45 to 55° C.

Meanwhile, the present application further provides a technical solution: the present application provides a method for preparing the above-mentioned crystal form B of the compound of formula (1), and the method comprises:

1) adding the compound of formula (1) to an alcohol solvent (for example, methanol, etc.) or a ketone solvent (for example, acetone, etc.) or a mixture thereof to dissolve, mixing with water, crystallizing, filtering to obtain a solid, and drying the resulting solid to give the crystal form B of the compound of formula (1); or
2) adding the compound of formula (1) to a halohydrocarbon solvent (for example, chloroform, etc.), volatilizing the solvent at room temperature to obtain a solid, and drying the resulting solid to give the crystal form B of the compound of formula (1); or
3) adding the compound of formula (1) to a hydrocarbon solvent (for example, methylbenzene, etc.), dissolving, stirring at room temperature, filtering to obtain a solid, and drying the resulting solid to give the crystal form B of the compound of formula (1); or
4) adding the compound of formula (1) to 2-methyltetrahydrofuran, stirring at a first set temperature, filtering and collecting a supernatant, and cooling the supernatant from the first set temperature to a second set temperature at a rate of 0.1±0.05° C./min and maintaining at the second set temperature, collecting a precipitated solid, and drying the resulting solid to give the crystal form B of the compound of formula (1), the first set temperature is 45 to 55° C., and the second set temperature is 0 to 10° C.

The present application further provides a method for preparing the crystal form C of the compound of formula (1): adding the compound of formula (1) to a mixture of tetrahydrofuran and a hydrocarbon solvent to form a turbid solution, stirring at a first set temperature, filtering and collecting a supernatant, and cooling the supernatant from the first set temperature to a second set temperature at a rate of 0.1±0.05° C./min and maintaining at the second set temperature, collecting a precipitated solid, and drying the resulting solid to give the crystal form C of the compound of formula (1), the set temperature is 45 to 55° C., and the second set temperature is 0 to 10° C.

The present application further provides a method for preparing the crystal form D of the compound of formula (1): adding the compound of formula (1) to a mixture of N-methyl-2-pyrrolidone and water to form a turbid solution, stirring at 45-55° C., filtering to obtain a solid, and drying the resulting solid to give the crystal form D of the compound of formula (1).

The present application further provides a method for preparing the crystal form E of the compound of formula (1), and the method comprises: dissolving the compound of formula (1) in N,N-dimethylacetamide, obtaining a solid by gas-liquid diffusion in the atmosphere of water or alcohol solvent, and filtering to give the crystal form E of the compound of formula (1).

The present application further provides a method for preparing the crystal form F of the compound of formula (1), and the method comprises: adding the compound of formula (1) to an ester solvent or an alcohol solvent or a mixture thereof to form a turbid solution, stirring at 0-10° C., filtering to obtain a solid, and drying the resulting solid to give the crystal form F of the compound of formula (1).

According to some specific and preferred aspects of the present application, the ester solvent may be ethyl acetate.

According to some specific and preferred aspects of the present application, the alcohol solvent may be methanol and/or ethanol.

According to some specific and preferred aspects of the present application, a stirring time may be 2-4 h.

In some preferred implementations (for example, in mass production of the crystal form F), before stirring the turbid solution at 0-10° C., heating the turbid solution to 30-60° C., and stirring at this temperature for more than 5 min, preferably more than 30 min, specifically, for example, 1-1.5 h. The particle size uniformity of the crystal form F product prepared in this way is better.

The present application further provides a pharmaceutical composition, which contains one or a combination of more of the above-mentioned crystals and a pharmaceutically acceptable carrier.

According to some specific and preferred aspects of the present application, the crystal of the compound of formula (1) is crystal form A, crystal form B, crystal form C, crystal form D, crystal form E, crystal form F, or is a single crystal form;

the crystal form A has an X-ray powder diffraction pattern with characteristic peaks at 2θ of 3.10°±0.2°, 8.74°±0.2°, 15.44°±0.2°, and 21.91°±0.2°;

the crystal form B has an X-ray powder diffraction pattern with characteristic peaks at 2θ of 8.42°±0.2°, 14.27°±0.2°, 16.04°±0.2°, and 25.41°±0.2°;

the crystal form C has an X-ray powder diffraction pattern with characteristic peaks at 2θ of 7.73°±0.2°, 17.13°±0.2°, 20.08°±0.2°, and 21.74°±0.2°;

the crystal form D has an X-ray powder diffraction pattern with characteristic peaks at 2θ of 7.94°±0.2°, 22.16°±0.2°, and 28.03°±0.2°;

the crystal form E has an X-ray powder diffraction pattern with characteristic peaks at 2θ of 8.01°±0.2°, 8.78°±0.2°, and 26.33°±0.2°;

the crystal form F has an X-ray powder diffraction pattern with characteristic peaks at 2θ of 5.77°±0.2°, 8.69°±0.2°, 17.48°±0.2°, and 22.84°±0.2°;

the single crystal form belongs to orthorhombic crystal system, with a space group of $P2_12_12_1$, and unit-cell parameters of which are: a=11.7±0.2 Å, b=19.6±0.2 Å, c=23.4±0.2 Å, α=90°±0.2°, β=90°±0.2°, γ=90°±0.2°.

The present application further provides use of the crystals in the preparation of anti-influenza virus drugs.

The present application further provides a method for preventing and/or treating a viral infection disease, wherein, the method comprises administering to an animal or human in need of prevention and/or treatment an effective amount of the crystals of the compound of formula (1).

According to some specific and preferred aspects of the present application, the viral infection disease is an infectious disease caused by influenza A virus and/or influenza B virus.

According to some specific and preferred aspects of the present application, the crystal of the compound of formula (1) is crystal form A, crystal form B, crystal form C, crystal form D, crystal form E, crystal form F, or is a single crystal form;

the crystal form A has an X-ray powder diffraction pattern with characteristic peaks at 2θ of 3.10°±0.2°, 8.74°±0.2°, 15.44°±0.2°, and 21.91°±0.2°;

the crystal form B has an X-ray powder diffraction pattern with characteristic peaks at 2θ of 8.42°±0.2°, 14.27°±0.2°, 16.04°±0.2°, and 25.41°±0.2°;

the crystal form C has an X-ray powder diffraction pattern with characteristic peaks at 2θ of 7.73°±0.2°, 17.13°±0.2°, 20.08°±0.2°, and 21.74°±0.2°;

the crystal form D has an X-ray powder diffraction pattern with characteristic peaks at 2θ of 7.94°±0.2°, 22.16°±0.2°, and 28.03°±0.2°;

the crystal form E has an X-ray powder diffraction pattern with characteristic peaks at 2θ of 8.01°±0.2°, 8.78°±0.2°, and 26.33°±0.2°;

the crystal form F has an X-ray powder diffraction pattern with characteristic peaks at 2θ of 5.77°±0.2°, 8.69°±0.2°, 17.48°±0.2°, and 22.84°±0.2°;

the single crystal form belongs to orthorhombic crystal system, with a space group of $P2_12_12_1$, and unit-cell parameters of which are: a=11.7±0.2 Å, b=19.6±0.2 Å, c=23.4±0.2 Å, α=90°±0.2°, β=90°±0.2°, γ=90°±0.2°.

The present application further provides a method for preventing and/or treating a viral infection disease, wherein, the method comprises administering to an animal or human in need of prevention and/or treatment an effective amount of the pharmaceutical composition.

According to some specific and preferred aspects of the present application, the viral infection disease is an infectious disease caused by influenza A virus and/or influenza B virus.

According to some specific and preferred aspects of the present application, the crystal of the compound of formula (1) is crystal form A, crystal form B, crystal form C, crystal form D, crystal form E, crystal form F, or is a single crystal form;

the crystal form A has an X-ray powder diffraction pattern with characteristic peaks at 2θ of 3.10°±0.2°, 8.74°±0.2°, 15.44°±0.2°, and 21.91°±0.2°;

the crystal form B has an X-ray powder diffraction pattern with characteristic peaks at 2θ of 8.42°±0.2°, 14.27°±0.2°, 16.04°±0.2°, and 25.41°±0.2°;

the crystal form C has an X-ray powder diffraction pattern with characteristic peaks at 2θ of 7.73°±0.2°, 17.13°±0.2°, 20.08°±0.2°, and 21.74°±0.2°;

the crystal form D has an X-ray powder diffraction pattern with characteristic peaks at 2θ of 7.94°±0.2°, 22.16°±0.2°, and 28.03°±0.2°;

the crystal form E has an X-ray powder diffraction pattern with characteristic peaks at 2θ of 8.01°±0.2°, 8.78°±0.2°, and 26.33°±0.2°;

the crystal form F has an X-ray powder diffraction pattern with characteristic peaks at 2θ of 5.77°±0.2°, 8.69°±0.2°, 17.48°±0.2°, and 22.84°±0.2°;

the single crystal form belongs to orthorhombic crystal system, with a space group of $P2_12_12_1$, and unit-cell parameters of which are: a=11.7±0.2 Å, b=19.6±0.2 Å, c=23.4±0.2 Å, α=90°±0.2°, β=90°±0.2°, γ=90°±0.2°.

In order to help understand the various embodiments disclosed in the present application, the following descriptions are provided:

The "solvate of the compound of formula (1)" is a substance formed by the interaction of the compound of formula (1) with a solvent through hydrogen bonds, salt bonds, and the like.

"A compound of the formula (1) in any form" includes any forms of the compound of the formula (1) such as amorphous, crystal, and solvate.

"Isomers" refer to compounds that have the same molecular formula but differ in the bonding properties or bonding sequence of their atoms or the spatial arrangement of their atoms. Isomers that differ in the spatial arrangement of their atoms are referred as "stereoisomers". Stereoisomers that are not mirrored to each other are referred as "diastereomers", and stereoisomers that are physical and mirrored to each other and non-superimposable are referred as "enantiomers". When the compound has an asymmetric center, for example, if a carbon atom is bonded to four different groups, there may be a pair of enantiomers. Enantiomers can be characterized by the absolute configuration of their asymmetric centers and described by the Cahn-Ingold-Prelog's R and S sequence rules, or described in terms of the way in which molecules rotate the plane of polarized light and are designated as dextrorotatory or levorotatory (i.e., (+) or (−) isomers, respectively). The methods for determining the absolute configuration of chiral compounds mainly comprises single crystal X-ray diffraction, nuclear magnetic resonance, and circular dichroism.

"Pharmaceutically acceptable carrier" refers to a carrier used for the administration of a therapeutic agent, and includes various excipients and diluents. This term refers to such pharmaceutical carriers: they are not essential active ingredients themselves, and they are not excessively toxic after administration. Suitable carriers are well known to those of ordinary skill in the art. A thorough discussion of pharmaceutically acceptable excipients can be found in Remington's Pharmaceutical Sciences (Mack Pub. Co., N. J. 1991). Pharmaceutically acceptable carriers in the composition may comprises liquids such as water, saline, glycerol, and ethanol. In addition, auxiliary substances such as disintegrants, wetting agents, emulsifiers, and pH buffer substances may also be present in these carriers.

The X-ray powder diffraction pattern is characteristic for a specific crystal form. When judging whether it is the same as the known crystal form, it should be noted that the relative positions of the peaks (i.e., 2θ) rather than their relative intensities. This is because the relative intensity of the pattern will change due to the dominant orientation effect caused by the difference in crystal conditions, particle size and other determination conditions, especially the low-intensity peak (intensity less than 20%) may not exist in some cases, the relative intensity of the diffraction peak is not characteristic for the determination of the crystal form, in fact, the relative intensity of the diffraction peak in the XRPD pattern is related to the preferred orientation of the crystal, the peak intensity shown herein is illustrative and not for absolute comparison. In addition, it is known in the art that when X-ray diffraction is used to determine the crystal of a compound, due to the influence of the measuring instrument or measuring conditions, the 2θ value of the same crystal form may have a certain measurement error, about ±0.2°. Therefore, this error should be taken into consideration when determining each crystal structure. In the XRD pattern, the peak position is usually expressed by the 2θ angle or the interplanar distance d value, and there is a simple conversion relationship between the two: d=λ/2 sin θ, where d represents the interplanar spacing d value, and λ represents the wavelength of incident X-rays, θ is the diffraction angle. It should also be pointed out that in the identification of the mixture, some diffraction lines will be missing due to factors such as decreased content. In addition, due to the influence of experimental factors such as sample height, the overall peak angle will be shifted, and a certain shift is usually allowed. Therefore, those skilled in the art can understand that the X-ray diffraction pattern of the crystal form referred to in the present application does not have to be exactly the same as the X-ray diffraction pattern in the example referred to here, and the "XRPD pattern is the same" as used herein does not mean absolutely the same, the same peak position can differ by ±0.2° (or greater error) and the peak intensity allows a certain variability. Any crystal form that has the same or similar pattern to the characteristic peaks in these patterns falls within the scope of the present application. Those skilled in the art can compare the patterns listed in the present application with the patterns of an unknown crystal form to confirm whether the two sets of patterns reflect the same or different crystal forms.

On the basis of specific X-ray crystal diffraction patterns, those skilled in the art are usually allowed to select several characteristic peaks to define the crystal form, and the selection of characteristic peaks can be comprehensively considered based on a certain purpose, and there is no strict limit, for example, those skilled in the art prefer to select peaks with relatively high intensity, peaks with relatively low-angle, and characteristic peaks with a relatively complete peak shape, and select characteristic peaks that are sufficiently distinguishable from other crystals, so that the characteristic peaks can be distinguished, identified and determined. Therefore, it cannot be concluded that a different crystal form is formed or it exceeds the crystal form range of the existing application just because the combination of the selected characteristic peaks is changed.

DSC measures the transition temperature when a crystal absorbs or releases heat due to a change in its crystal structure or melting of the crystal. For the same crystal form of the same compound, in continuous analysis, the error of thermal transition temperature and melting point is typically within about 5° C. When we say that a compound has a given DSC peak or melting point, this means that the DSC peak or melting point is ±5° C. It should be pointed out that for a mixture, its DSC peak or melting point may vary in a larger range. In addition, due to the decomposition of the substance in the process of melting, the melting temperature is related to the heating rate.

It should be noted that the numerical values and numerical ranges mentioned in the present application should not be construed narrowly as numerical values or numerical ranges themselves, those skilled in the art should understand that they can fluctuate around specific values based on different specific technical environments without departing from the spirit and principles of the present application.

Due to the implementation of the above technical solutions, the present application has the following advantages over the prior art:

the present application provides a novel pyridone derivative, and this compound has high bioavailability, can be transformed into a compound with strong inhibitory activity against influenza virus type A and influenza virus type B after being taken by the human body, and can be individually used for clinical treatment or in combination with other anti-influenza drugs such as neuraminidase inhibitors, nucleoside drugs, and PB2 inhibitors, is capable of clinically curing influenza patients quickly, and it is superior to existing pyridone derivatives in at least one of activity, pharmacokinetics properties (such as bioavailability), and cytotoxicity. Meanwhile, the crystals of the compound of formula (1) or solvates thereof provided in the present application meet the requirements for pharmaceutical use in the terms of stability, hygroscopicity, solubleness and storability, etc., and is suitable for use in preparing medicines for treating influenza.

DETAILED DESCRIPTION OF EXEMPLARY EMBODIMENTS

Figure 1:
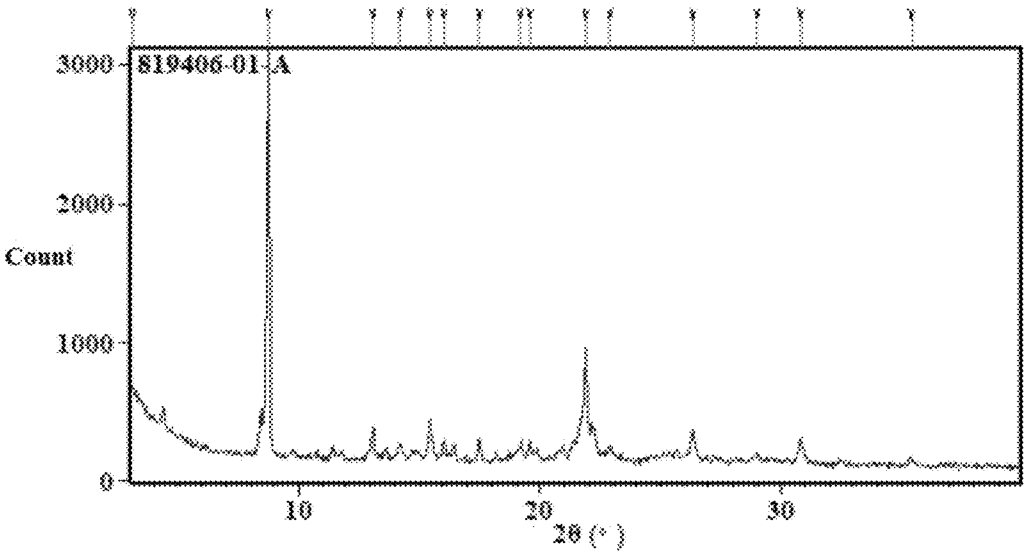
FIG. 1 is an XRPD pattern of the crystal form A of the compound of formula (1) prepared in Embodiment 3.

The "room temperature" mentioned in the present application refers to the temperature of the natural environment that can be reached without additional heating or cooling, and the corresponding specific temperature may be between 10-30° C.

In the present application, the test instruments and conditions used in the experiment are as follows:

1. Single Crystal X-Ray Diffraction
   - Instrument model: Bruker D8 Venture single-crystal diffractometer
   - Light source: Mo target
   - X-ray: Mo—K (=0.71073 Å)
   - Detector: CMOS based detector
   - Resolution: 0.84 Å
   - Current and voltage: 50 kV, 1.4 A
2. X-Ray Powder Diffraction (XRPD)
   - Instrument model: PANalytical X'Pert3 Power
   - X-ray: Cu, Kα, Kα1 (Å): 1.540598; Kα2 (Å): 1.544426
   - X-ray tube setting: 45 kV, 40 mA
   - Divergence slit: 1/8°
   - Scan pattern: continuous
   - Scanning range (2θ): 3°-40°
   - Scan step size (2θ): 0.0263°

3. Differential Scanning Calorimetry (DSC)
   - Instrument model: TA Q2000/2500 differential scanning calorimeter
   - Heating rate: 10° C./min
   - Temperature range: 25° C. to setting end-point temperature
   - Shielding gas: nitrogen
4. Thermogravimetric Analysis (TGA)
   - Instrument model: TA Q5000/5500 thermogravimetric analyzer
   - Heating rate: 10° C./min
   - Temperature range: room temperature to setting end-point temperature
   - Shielding gas: nitrogen
5. Dynamic Vapour Sorption (DVS)
   - Instrument model: SMS DVS Intrinsic vapour sorption analyzer
   - Temperature: 25° C.
   - RH range: 0% RH-95% RH
   - Shielding gas: nitrogen The application will be further explained below in conjunction with specific embodiments.

Embodiment 1: Preparation of the Compound of Formula (1)

The route is as follows:

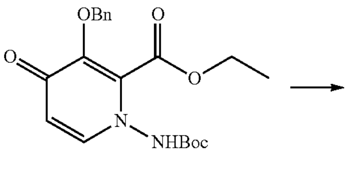

(11)

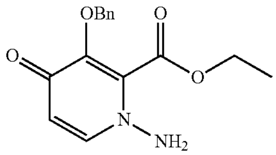

(10)

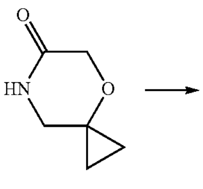

(9)

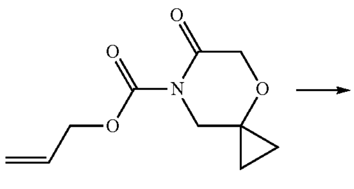

(8)

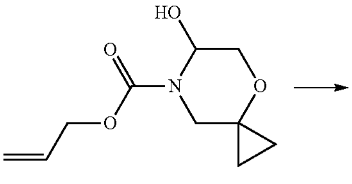

(7)

-continued

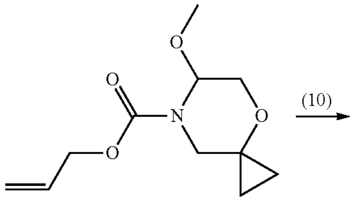

(6)

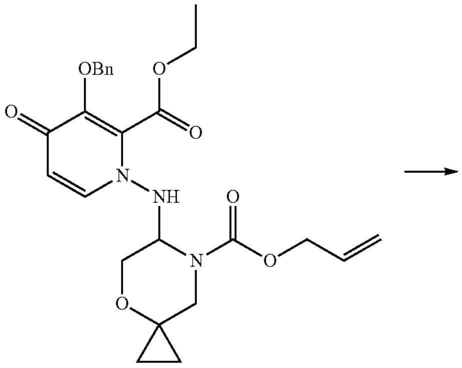

(5)

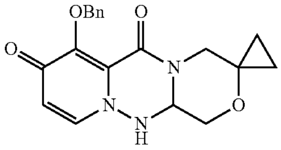

(4)

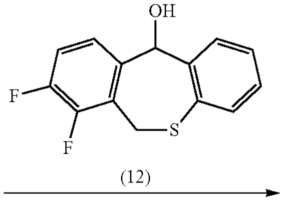

(12)

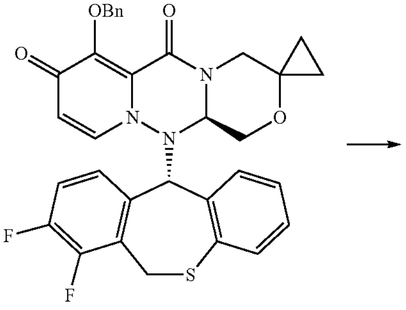

(3)

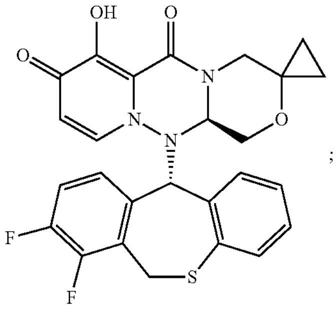

;

(2)

-continued

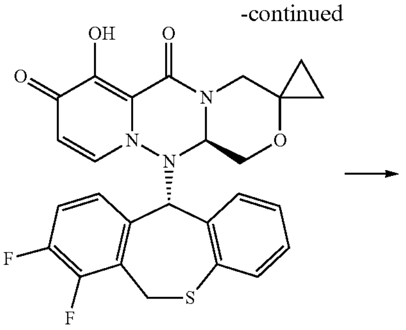

(2)

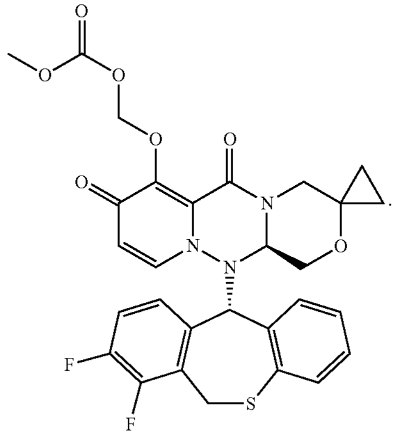

(1)

Preparation of Compound of formula (10): Compound of formula (11) (388 mg, 1 mmol) was dissolved in 3 mL dichloromethane and added with 1 mL trifluoroacetic acid, and the mixture was stirred at room temperature for 3 hours. TLC showed the reaction was complete, and the mixture was added with 3N sodium hydroxide solution to adjust pH=9-10. The mixture was extracted with dichloromethane, and organic phases were merged, washed with saturated salt solution, dried, and concentrated to give 270 mg solid, which was directly used in the next step.

Preparation of Compound of formula (8): Compound of formula (9) (1.0 g, 7.8 mmol) was dissolved in 10 mL anhydrous tetrahydrofuran, and dropwise added with 2.5M n-butyllithium solution (3.1 mL, 7.8 mmol) slowly at −78° C. and under nitrogen protection. After addition, the mixture was stirred and reacted at the temperature for 2 hours. Then allyl formate (0.94 g, 7.8 mmol) was dropwise added. After addition, the mixture was stirred and reacted for 2 hours, and TLC showed the raw materials were substantially completely reacted, and then the reaction mixture was poured into saturated ammonium chloride solution to quench, and then extracted with ethyl acetate (15 mL×3). The organic phases were merged, dried over anhydrous sodium sulfate, and concentrated to dry to give 1.65 g oily product.

Preparation of Compound of formula (7): Compound of formula (8) (1.65 g, 7.8 mmol) was dissolved in 15 mL anhydrous tetrahydrofuran, and dropwise added with 1M diisobutylaluminum hydride solution (11.7 mL, 11.7 mmol) slowly at −78° C. and under nitrogen protection. After addition, the mixture was stirred and reacted at the temperature for 2 hours. TLC showed the raw materials were substantially completely reacted, and then the reaction mixture was poured into saturated potassium sodium tartrate solution to quench, and then extracted with ethyl acetate (20 mL×3). The organic phases were merged, dried over anhydrous sodium sulfate, and concentrated to dry to give 1.57 g oily product.

Preparation of Compound of formula (6): Compound of formula (7) (1.57 g, 7.4 mmol) was dissolved in 15 mL methanol, and p-toluenesulfonic acid monohydrate (140 mg, 0.74 mmol) was added, and the mixture was stirred at room temperature overnight. TLC showed the raw materials were substantially completely reacted, and then the mixture was added with saturated sodium bicarbonate solution to adjust to be neutral, and concentrated. The residue was separated by column chromatography to give 0.86 g yellow oily product.

Preparation of Compound of formula (5): Compound of formula (10) (270 mg, 0.94 mmol) and Compound of formula (6) (255 mg, 1.13 mmol) were dissolved in 5 mL acetonitrile. 1M solution of tin tetrachloride in dichloromethane (1.4 mL, 1.41 mmol) was added dropwise under nitrogen protection and at −20° C. After addition, the mixture was stirred and reacted at the temperature for 3 hours. The mixture was added with saturated sodium bicarbonate solution, stirred for 30 min, and stood to layer, and the aqueous phase was extracted with dichloromethane. The organic phases were merged, washed with saturated salt solution, dried, and concentrated to give 428 mg crude product.

Preparation of Compound of formula (4): Compound of formula (5) (428 mg, 0.89 mmol) was dissolved in 5 mL tetrahydrofuran, and tetrakis(triphenylphosphine)palladium (104 mg, 0.09 mmol) and morpholine (774 mg, 8.9 mmol) were added and reacted at room temperature for 2 hours. The reaction was shown complete through TLC spot plate analysis. The mixture was concentrated, and the residue was separated by column chromatography to give 216 mg product.

Preparation of Compound of formula (3): Compound of formula (4) (216 mg, 0.61 mmol) and Compound of formula (12) (242 mg, 0.92 mmol) were reacted at 100° C. for 3 hours in 3 mL solution of $T_3P$ in ethyl acetate under airtight condition. The mixture was cooled, diluted with saturated $NaHCO_3$, and then extracted with ethyl acetate. The organic phases were merged, dried and concentrated, and separated by column chromatography to give 200 mg crude product, which was separated by chiral column to give 40 mg product.

Preparation of Compound of formula (2): Compound of formula (3) (40 mg, 0.067 mmol) and lithium chloride (20 mg, 0.48 mmol) were reacted at 100° C. for 3 hours in 1 mL DMA. After the reaction finished, the mixture was diluted with 10 mL water, and added with 2N hydrochloric acid to adjust pH to 3-4. The mixture was filtered, and the solid was pumped to dry to give 25 mg product. $^1$HNMR (400 MHz, $CDCl_3$) δ: 7.05-7.15 (m, 5H), 6.85 (m, 1H), 6.70 (d, 1H, J=7.6 Hz), 5.78 (d, 1H, J=7.6 Hz), 5.3 (m, 2H), 4.69 (d, 1H, J=6.8 Hz), 4.17 (d, 1H, J=14 Hz), 4.09 (d, 1H, J=14 Hz), 3.90 (m, 1H), 3.69 (m, 1H), 3.44 (d, 1H, J=15.2 Hz), 0.95 (m, 1H), 0.74 (m, 3H); ESI-MS m/z $(M+H)^+$ 510.1.

Preparation of Compound of formula (1): Compound of formula (2) (40 mg, 0.08 mmol), chloromethyl methyl carbonate (25 mg, 0.2 mmol), potassium carbonate (28 mg, 0.2 mmol) and potassium iodide (3 mg, 0.02 mmol) were reacted at 60° C. for 5 hours in 1 mL N,N-dimethylacetamide. The reaction was shown complete through TLC spot plate analysis, the mixture was added with water to quench, and added with 1N diluted hydrochloric acid to adjust pH to 3-4. The solid was filtered, dried, and separated by column chromatography to give 35 mg product, which was the compound of formula (1), and the solid was analyzed to be amorphous and used as the starting material for preparing various crystal forms in subsequent embodiments. $^1$HNMR (400 MHz, DMSO-d6) δ: 7.40-7.42 (m, 2H), 7.25 (d, 1H, J=7.6 Hz), 7.15 (m, 1H), 7.10 (m, 1H), 7.00 (d, 1H, J=7.2 Hz), 6.84 (t, 1H, J=7.6 Hz), 5.75 (m, 4H), 5.43 (d, 1H, J=16.4 Hz), 4.57 (dd, 1H, J=3.2, 9.6 Hz), 3.96-4.03 (m, 3H), 3.73 (s, 3H), 3.51 (t, 1H, J=10.0 Hz), 3.41 (s, 1H), 0.75 (t, 2H, J=8.4 Hz), 0.50 (m, 2H); ESI-MS m/z $(M+H)^+$ 598.1.

Embodiment 2: Pharmacodynamic Experiment of the Compound of Formula (1)

2.1 In Vitro Bioactivity and Cytotoxicity Study

In actual drug applications, the compound of formula (1) is a prodrug of the compound of formula (2), and is converted into an active drug (the compound of formula (2)) in the body to exert its efficacy. For the activity data and toxicity data of the compound of formula (2), see Table a.

Test method for In vitro bioactivity study: MDCK cells were seeded into 384-well cell culture plate at a density of 2,000 cells/well, and then incubated at 37° C. overnight in a 5% $CO_2$ incubator. On the following day, the compounds were diluted and added into the wells (3-fold multiple proportion dilution, 8 test concentration points), and the influenza virus A/PR/8/34 (H1N1) strain was then added to the cell culture wells at 2*TCID90 per well, and the final concentration of DMSO in the medium was 0.5%. The cell plate was incubated at 37° C. for 5 days in the 5% $CO_2$ incubator. After 5 days of culture, the cell viability was measured using the cell viability detection kit CCK8. The raw data were subjected to nonlinear fitting analysis of the inhibition rate and cytotoxicity of the compounds using GraphPad Prism software to obtain $EC_{50}$ values (see Table a for the results).

Method for cytotoxicity study: the cytotoxicity assay and antiviral activity assay of the compounds were performed in parallel, except for the absence of virus, other experimental conditions were consistent with the antiviral activity assay. After 5 days of culture, the cell viability was measured using the cell viability detection kit CCK8. Raw data were used for calculating compound cytotoxicity ($CC_{50}$) (see Table a for results).

TABLE a

| Inhibitory activity and toxicity of the compounds against influenza virus A/PR/8/34 (H1N1) Results (nM) | | |
|---|---|---|
| | $EC_{50}$ | $CC_{50}$ |
| Compound of formula (2) | 0.26 | >1000 |
| Comparative compound Baloxavir acid | 1.4 | >1000 |

The results showed that when compared with the comparative compound, the compound of the present application has more excellent activity against H1N1 and has low cytotoxicity.

2.2 Rat PK Study

Intravenous injection: about 2 mg of samples, namely the compound of formula (2) was accurately weighed, appropriate amount of DMA was added, and the system was vortex oscillated to completely dissolve the solid matter; an appropriate volume of 30% Solutol HS-15 aqueous solution was added, and the system was vortex oscillated and then saline was added such that DMA: 30% Solutol HS-15: saline=20:20:60 (v/v/v), the liquid was vortex oscillated to mix evenly, and filtered to give a pharmaceutical preparation of a concentration of 0.05 $mg \cdot mL^{-1}$. SD rats were given a single intravenous injection of 0.25 $mg \cdot mL^{-1}$ of the compound of formula (2) intravenously. 0.20 mL of blood was collected from the jugular vein before administration and 0.083 h, 0.25 h, 0.5 h, 1 h, 2 h, 4 h, 8 h, 12 h and 24 h after administration, and placed in an EDTA-$K_2$ anticoagulation tube. 150 μL of whole blood was accurately aspirated immediately, and added into a test tube to which 450 μL of acetonitrile has been added to precipitate proteins, and the tube was vortex oscillated, and placed on wet ice. It was stored in a −90∼−60° C. refrigerator for biological sample analysis. The concentration of the corresponding compound in the plasma of S-D rats was determined by LC-MS/MS analysis. The corresponding pharmacokinetic parameters were calculated using a non-compartmental model in Pharsight Phoenix 7.0. See Table b for the results.

Gavage administration: about 4 mg of sample, the compound of formula (1) was accurately weighed, appropriate amount of PEG400 was added, and the system was vortex oscillated to completely dissolve the solid matter; an appropriate volume of 30% Solutol HS-15 aqueous solution was added, the system was vortex oscillated and then saline was added such that PEG400: 30% Solutol HS-15: saline=2:2:6 (v/v/v), the liquid was vortex oscillated to mix evenly, to give a pharmaceutical preparation of a concentration of 0.3 $mg \cdot mL^{-1}$. SD rats were given a single oral administration of 3.0 $mg \cdot mL^{-1}$ of the compound of formula (1) by gavage, and the concentration of the compound of formula (2) in the plasma of S-D rats was measured before administration and 0.25 h, 0.5 h, 1 h, 2 h, 4 h, 8 h, 12 h and 24 h after administration. See Table c for the results.

TABLE b

| PK Parameters (Intravenous Injection) of the Compound of formula (2) | |
|---|---|
| PK (i.v.) | Compound of formula (2) |
| $T_{1/2}$ (h) | 2.97 |
| $AUC_{0-t}$ ($ng \cdot h \cdot mL^{-1}$) | 276 |
| CL ($mL \cdot kg^{-1} \cdot min^{-1}$) | 13.6 |
| $Vd_{ss}$ ($L \cdot kg^{-1}$) | 3.12 |

TABLE c

| PK Parameters (Gavage) of the Tested Compound of formula (1) | |
|---|---|
| PK (i.g.) | Compound of formula (1) |
| $T_{1/2}$ (h) | 3.32 |
| $T_{max}$ (h) | 1.67 |
| $C_{max}$ ($ng \cdot mL^{-1}$) | 253 |
| $AUC_{0-t}$ ($ng \cdot h \cdot mL^{-1}$) | 1377 |
| F (%) | 47.2 |

The above results indicate that the compound of formula (1) of the present application have a low in vivo clearance rate, has a long half-life, high bioavailability, and has high absorption in the body.

2.3 Efficacy on Mice

Female BALB/c mice were inoculated with influenza A virus (H1N1, A/WSN/33) by intranasal administration to establish an IAV mouse infection model. Menstruum, the compound of formula (1) (15 mpk) or oseltamivir phosphate (15 mpk) were orally administered twice a day. Animal weight and survival status were monitored daily during the test, and on the 5th day, some animals were sacrificed to take lung tissue for virus titer detection, and the remaining mice were used for survival rate monitoring. The in vivo anti-influenza virus efficacy of the test compound was determined by virus titer in lung tissue, mouse body weight change and survival rate.

Virus titer in lung tissue: on the 5th day after virus infection, the average virus titer in the lung tissue of mice in the menstruum group reached 7.20 Log 10 (number of plaques per gram of lung tissue), the average virus titer in the lung tissue of mice in the oseltamivir phosphate group was 3.74 Log 10 (number of plaques per gram of lung tissue). Compared with the menstruum group, oseltamivir phosphate significantly inhibited the replication of the virus in mice, and the average virus titer decreased by 3.46 Log 10 (number of plaques per gram of lung tissue), and the difference was very statistically significant ($p<0.01$) between the results, showing the expected efficacy; the average virus titer in the lung tissue of mice on the 5th day after treatment with test compound of formula (1) was 3.28 Log 10 (number of plaques per gram of lung tissue)), and compared with the menstruum group, the test compound significantly inhibited the replication of the virus in mice, and the average virus titer decreased by 3.92 Log 10 (number of plaques per gram of lung tissue), and the difference was extremely statistically significant ($p<0.001$) between the results, which is superior to the control compound oseltamivir phosphate (Table d).

TABLE d

Virus Titer in Lung Tissue

| Group | Influenza virus titer Log10 (plaques number/gram of lung) | Statistical analysis (Compared with the menstruum group) Mean difference | Statistic difference |
|---|---|---|---|
| Menstruum | 7.20 ± 0.1024 | NA | NA |
| Oseltamivir phosphate | 3.74 ± 0.5205 | 3.46 | **($p < 0.01$) |
| Compound of formula (1) | 3.28 ± 0.2813 | 3.92 | ***($p < 0.001$) |

**$P < 0.01$ means very significant difference,
***$P < 0.001$ means extremely significant difference Body weight change and result analysis: the mice in the menstruum group showed significant weight loss on the 3rd day after infection, and then continued to decline or even die; the weight of the mice in the oseltamivir phosphate group and the compound of formula (1) group remained stable during the experiment, had no significant decline, and the mice were in good health.

Survival rate and result analysis: the mice in the menstruum group were found dead on the 7th day after infection, and on the 10th day, all mice died or were euthanized due to weight loss to the humane end point, and the survival rate was 0%; the mice in the oseltamivir phosphate group and in the compound of formula (1) group maintained healthy during the experiment, and all animals survived to the predetermined experimental end point with a survival rate of 100%, indicating excellent anti-influenza efficacy in vivo.

Embodiment 3: Preparation of the Crystal Form A of the Compound of Formula (1)

Method 1: 15 mg of the compound of formula (1) was weighted, and completely dissolved in 1 mL of isopropyl acetate. 4 mL of n-heptane was slowly added to the clear solution while stirring, and a solid was precipitated. The system was stirred for 1 h and filtered, and the solid was forced-air dried at 50° C. for 4 h, to give 13.6 mg product, with a yield of 90.7% and an HPLC purity of 99.3%.

Method 2: 15 mg of the compound of formula (1) was weighted, and completely dissolved in 1 mL of ethyl acetate. To a 20 mL bottle, 4 mL of n-heptane was added, and the solution of the compound in ethyl acetate was slowly added into the n-heptane while stirring, and a solid was precipitated. The system was stirred for 1 h and filtered, and the solid was forced-air dried at 50° C. for 4 h, to give 14.0 mg product, with a yield of 93.3% and an HPLC purity of 99.1%.

Method 3: 15 mg of the compound of formula (1) was weighted, and completely dissolved in 1 mL of acetone, then the solvent was volatilized at room temperature, and the solid was collected and forced-air dried at 50° C. for 4 h.

Method 4: 15 mg of the compound of formula (1) was weighted, and 0.5 mL of methyl tert-butyl ether was added, then the resulting turbid solution was magnetically stirred at room temperature for 3 days, and centrifuged to collect the solid, and the solid was forced-air dried at 50° C. for 4 h.

Method 5: 15 mg of the compound of formula (1) was weighted, and 0.5 mL of water was added, then the resulting turbid solution was magnetically stirred at 50° C. for 3 days, and centrifuged to collect the solid, and the solid was forced-air dried at 50° C. for 4 h.

Method 6: 15 mg of the compound of formula (1) was weighted, and 0.1 mL of methylbenzene and 0.4 mL of methyl tert-butyl ether were added, then the resulting turbid solution was magnetically stirred at 50° C. for 2 h, and the sample was place in a biochemical incubator, the temperature was increased and decreased at a rate of 0.1° C./min, and 50-5° C. temperature rise-fall cycle test was performed for three times. The sample was finally stirred at 5° C., and centrifuged to collect the solid, and the solid was forced-air dried at 50° C. for 4 h.

XRPD test was performed on the solid obtained in Method 1, and the pattern is shown in FIG. 1, there are characteristic peaks at diffraction angles $2\theta$=3.10, 8.74, 13.08, 15.44, 21.91, 26.35, and 30.83 degrees, and the $2\theta$ error range is ±0.2 degrees. Its x-ray powder diffraction data are shown in Table 1.

Figure 2:
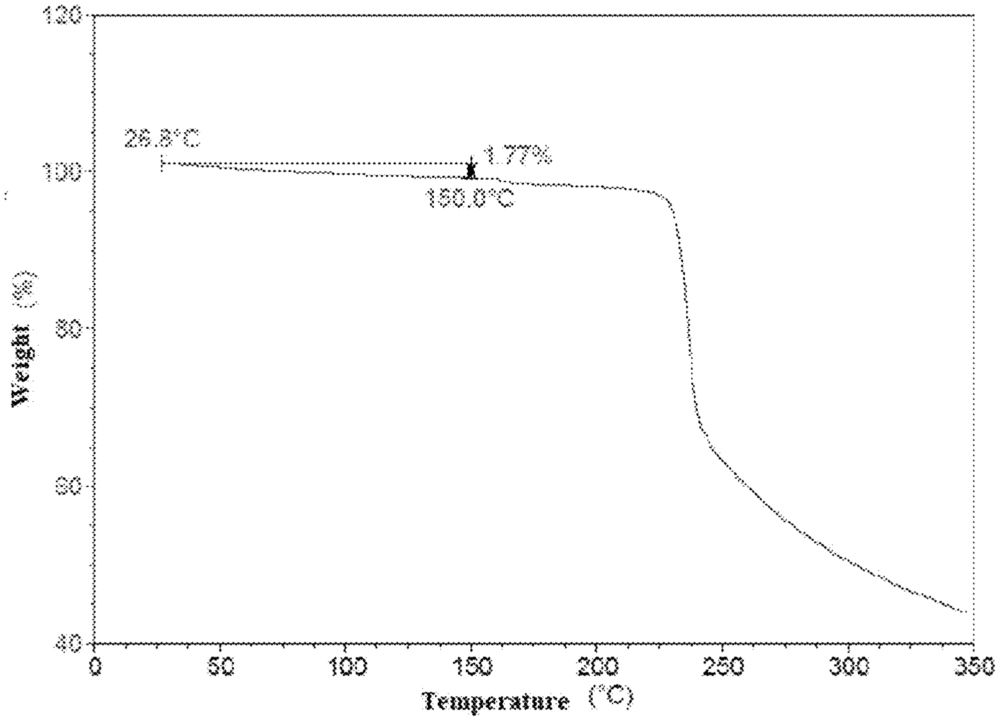
FIG. 2 is a TGA spectrum of the crystal form A of the compound of formula (1) prepared in Embodiment 3.
Figure 3:
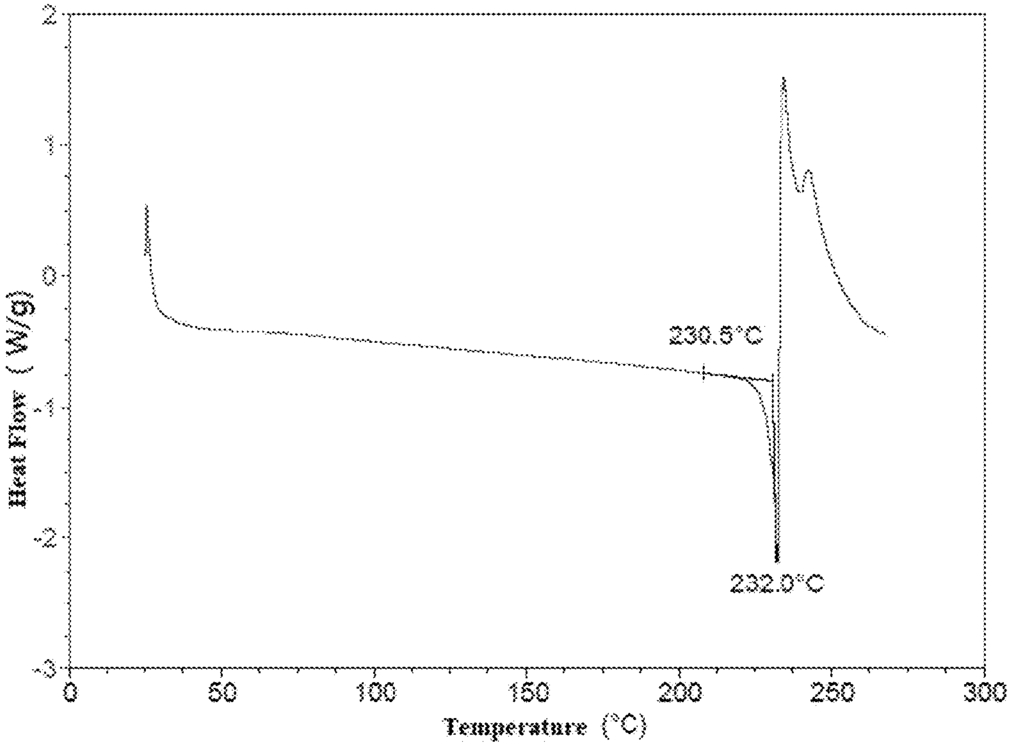
FIG. 3 is a DSC spectrum of the crystal form A of the compound of formula (1) prepared in Embodiment 3.

The results of TGA (FIG. 2) and DSC (FIG. 3) show that the sample has a weight loss of 1.8% when heated to 150° C., and has an endothermic peak at 232.0° C. (peak value), and the crystal form A of the compound of formula (1) is anhydrous crystal form.

TABLE 1

XRPD pattern details of the crystal form A of the compound of formula (1)

| Position [$2\theta$ (°)] | D spacing [Å] | Relative intensity [%] |
|---|---|---|
| 3.10 | 28.50 | 8.72 |
| 8.74 | 10.12 | 100.00 |
| 13.08 | 6.77 | 7.10 |
| 14.20 | 6.24 | 3.17 |
| 15.44 | 5.74 | 9.68 |
| 16.03 | 5.53 | 4.68 |
| 17.50 | 5.07 | 5.34 |
| 19.20 | 4.62 | 3.75 |
| 19.58 | 4.53 | 4.61 |
| 21.91 | 4.06 | 28.01 |
| 22.89 | 3.89 | 2.91 |

TABLE 1-continued

| XRPD pattern details of the crystal form A of the compound of formula (1) | | |
|---|---|---|
| Position [2θ (°)] | D spacing [Å] | Relative intensity [%] |
| 26.35 | 3.38 | 7.05 |
| 30.83 | 2.90 | 6.21 |

XRPD tests were performed on the solids obtained by other methods, and the test patterns were substantially the same as depicted in FIG. 1, indicating that the obtained solids were the crystal form A of the compound of formula (1).

Embodiment 4: Preparation of the Crystal Form B of the Compound of Formula (1)

Method 1: 15 mg of the compound of formula (1) was weighted, and completely dissolved in 1 mL of methanol. 4 mL of water was slowly added to the clear solution while stirring, and a solid was precipitated. The system was stirred for 1 h and filtered, and the solid was forced-air dried at 50° C. for 4 h, to give 14.1 mg product, with a yield of 94% and an HPLC purity of 99.2%.

Method 2: 15 mg of the compound of formula (1) was weighted, and completely dissolved in 1 mL of acetone. To a 20 mL bottle, 4 mL of water was added, and the solution of the compound in acetone was slowly added into the water while stirring, and a solid was precipitated. The system was stirred for 1 h and filtered, and the solid was forced-air dried at 50° C. for 4 h, to give 13.8 mg product, with a yield of 92% and an HPLC purity of 99.2%.

Method 3: 15 mg of the compound of formula (1) was weighted, and completely dissolved in 1 mL of chloroform, then the solvent was volatilized at room temperature, and the solid was collected and forced-air dried at 50° C. for 4 h.

Method 4: 15 mg of the compound of formula (1) was weighted, and 0.5 mL of methylbenzene was added, then the resulting turbid solution was magnetically stirred at room temperature for 3 days, and centrifuged to collect the solid, and the solid was forced-air dried at 50° C. for 4 h.

Method 5: 15 mg of the compound of formula (1) was weighted, and 0.5 mL of 2-methyltetrahydrofuran was added, then the resulting turbid solution was stirred at 50° C. for 2 h, and filtered to collect the supernatant. The supernatant was cooled from 50° C. to 5° C. at a rate of 0.1° C./min, and maintained at 5° C. The precipitated solid was collected, and forced-air dried at 50° C. for 4 h.

Figure 4:
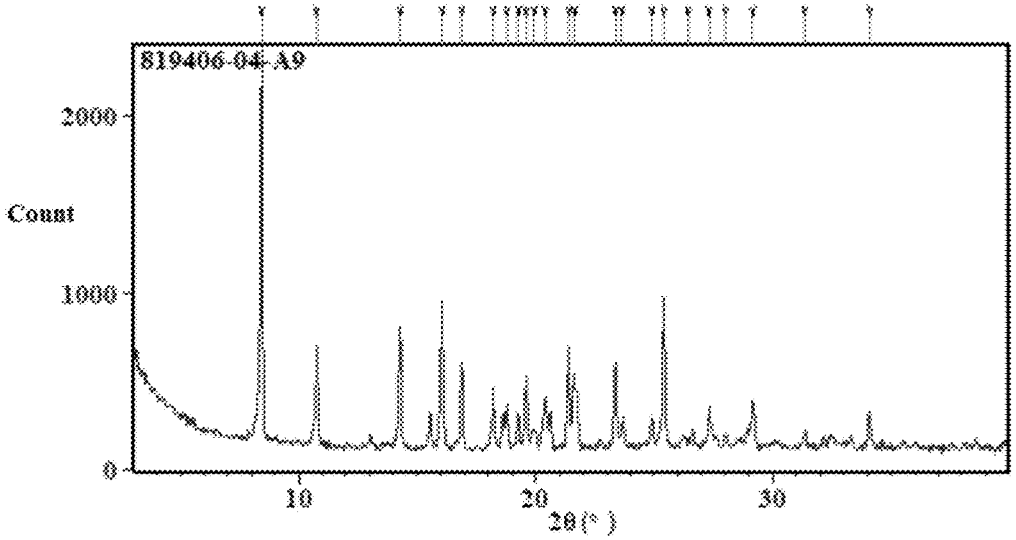
FIG. 4 is an XRPD pattern of the crystal form B of the compound of formula (1) prepared in Embodiment 4.

XRPD test was performed on the solid obtained in Method 1, and the pattern is shown in FIG. 4, there are characteristic peaks at diffraction angles 2θ=8.42, 10.75, 14.27, 16.04, 16.87, 19.60, 20.40, 21.39, 21.66, 23.38, 25.41, 27.32, 29.17 and 34.08 degrees, and the 2θ error range is ±0.2 degrees. Its x-ray powder diffraction data are shown in Table 2.

Figure 5:
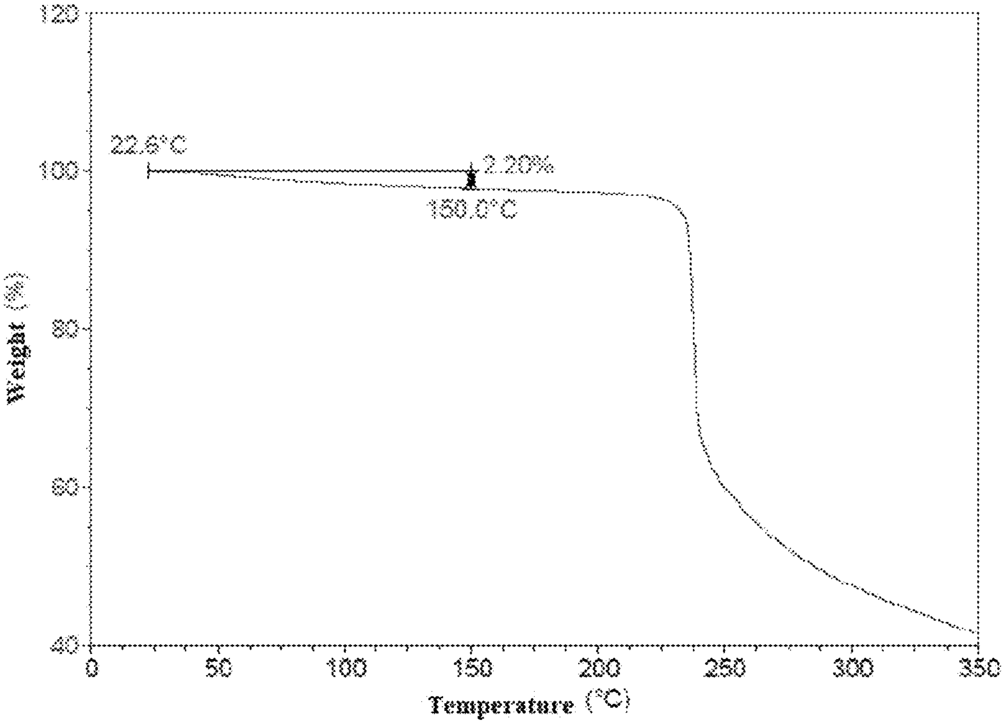
FIG. 5 is a TGA spectrum of the crystal form B of the compound of formula (1) prepared in Embodiment 4.
Figure 6:
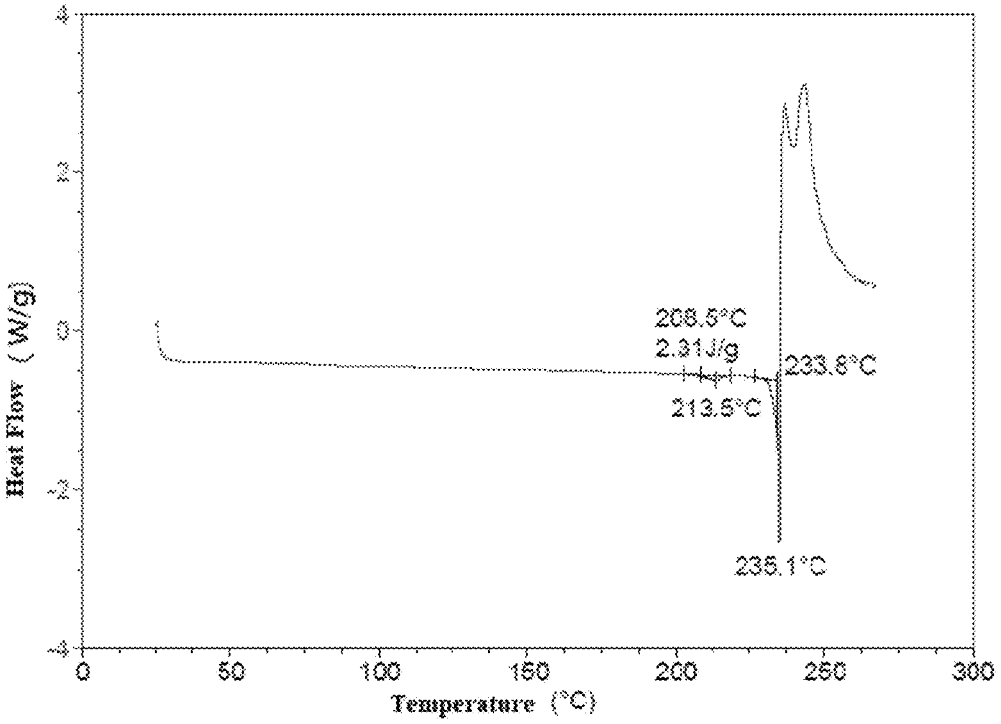
FIG. 6 is a DSC spectrum of the crystal form B of the compound of formula (1) prepared in Embodiment 4.

The results of TGA (FIG. 5) and DSC (FIG. 6) show that the sample has a weight loss of 2.2% when heated to 150° C., and has two endothermic peaks at 213.5° C. and 231.5° C. (peak values), and the crystal form B of the compound of formula (1) is anhydrous crystal form.

TABLE 2

| XRPD pattern details of the crystal form B of the compound of formula (1) | | |
|---|---|---|
| Position [2θ (°)] | D spacing [Å] | Relative intensity [%] |
| 8.42 | 10.50 | 100.00 |
| 10.75 | 8.23 | 27.14 |
| 14.27 | 6.21 | 36.91 |
| 16.04 | 5.53 | 44.93 |
| 16.87 | 5.25 | 26.64 |
| 18.21 | 4.87 | 18.81 |
| 18.78 | 4.72 | 13.79 |
| 19.26 | 4.61 | 11.00 |
| 19.60 | 4.53 | 22.26 |
| 19.92 | 4.46 | 5.65 |
| 20.40 | 4.35 | 15.37 |
| 21.39 | 4.15 | 25.90 |
| 21.66 | 4.10 | 19.03 |
| 23.38 | 3.81 | 26.50 |
| 23.67 | 3.76 | 7.85 |
| 24.91 | 3.58 | 9.49 |
| 25.41 | 3.50 | 43.22 |
| 27.32 | 3.26 | 13.04 |
| 28.01 | 3.19 | 4.24 |
| 29.17 | 3.06 | 11.55 |
| 31.35 | 2.85 | 4.60 |
| 34.08 | 2.63 | 11.15 |

XRPD tests were performed on the solids obtained by other methods, and the test patterns were substantially the same as depicted in FIG. 4, indicating that the obtained solids were the crystal form B of the compound of formula (1).

Embodiment 5: Preparation of the crystal form C of the compound of formula (1)

Method: 15 mg of the compound of formula (1) was weighted, and 0.25 mL of tetrahydrofuran and 0.25 mL of n-heptane were added, then the resulting turbid solution was stirred at 50° C. for 2 h, and filtered to collect the supernatant. The supermatant was cooled from 50° C. to 5° C. at a rate of 0.1° C./min, and maintained at 5° C. The precipitated solid was collected, and forced-air dried at 50° C. for 4 h.

Figure 7:
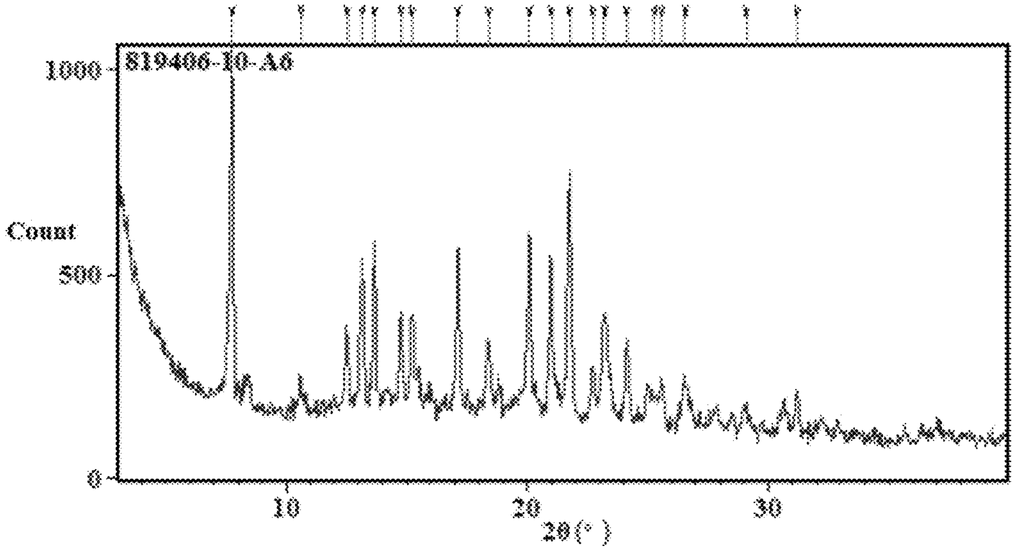
FIG. 7 is an XRPD pattern of the crystal form C of the compound of formula (1) prepared in Embodiment 5.

XRPD test was performed on the solid obtained in the above-mentioned method, and the pattern is shown in FIG. 7, there are characteristic peaks at diffraction angles 2θ=7.73, 12.51, 13.13, 13.65, 14.76, 15.21, 17.13, 18.39, 20.08, 20.98, 21.74, 23.22 and 24.13 degrees, and the 2θ error range is ±0.2 degrees. Its x-ray powder diffraction data are shown in Table 3.

Figure 8:
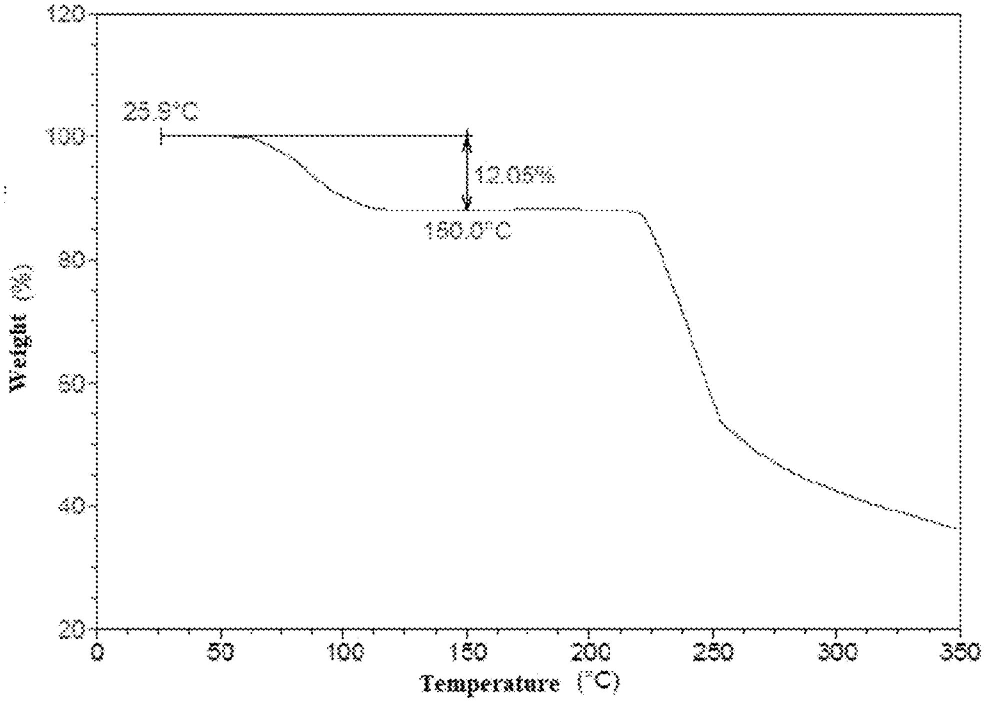
FIG. 8 is a TGA spectrum of the crystal form C of the compound of formula (1) prepared in Embodiment 5.
Figure 9:
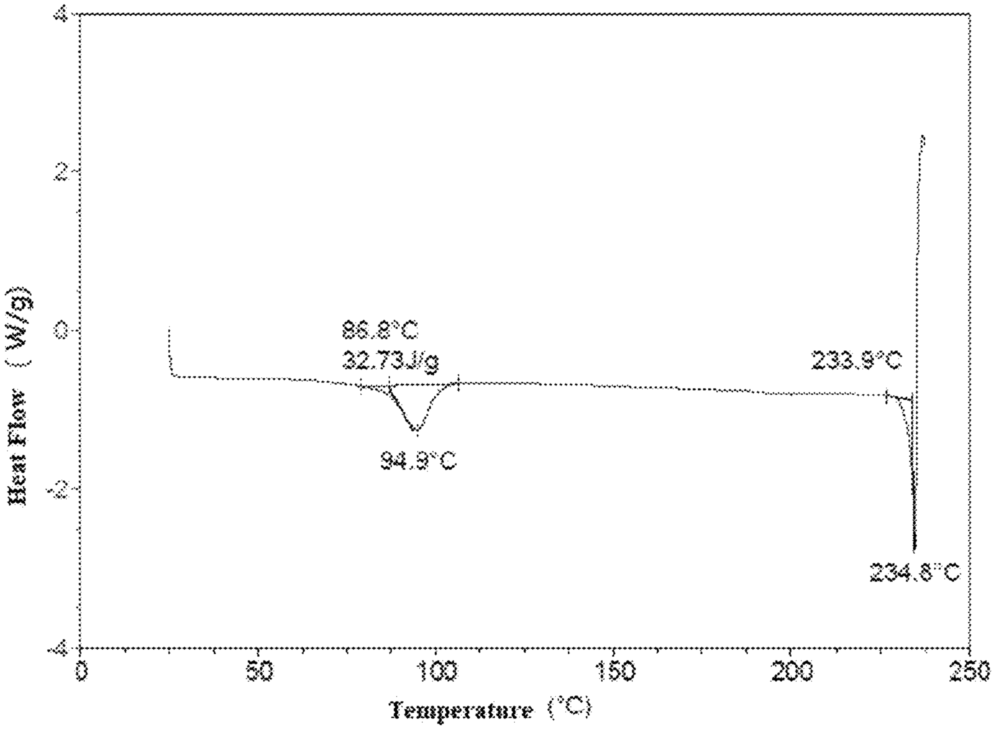
FIG. 9 is a DSC spectrum of the crystal form C of the compound of formula (1) prepared in Embodiment 5.

The results of TGA (FIG. 8) and DSC (FIG. 9) show that the sample has a weight loss of 12.1% when heated to 150° C., and has two endothermic peaks at 94.9° C. and 234.8° C. (peak values), and the crystal form C of the compound of formula (1) is a THF solvate.

TABLE 3

| XRPD pattern details of the crystal form C of the compound of formula (1) | | |
|---|---|---|
| Position [2θ (°)] | D spacing [Å] | Relative intensity [%] |
| 7.73 | 11.43 | 100.00 |
| 10.61 | 8.34 | 7.14 |
| 12.51 | 7.08 | 24.74 |
| 13.13 | 6.74 | 40.04 |
| 13.65 | 6.49 | 47.88 |
| 14.76 | 6.00 | 29.00 |
| 15.21 | 5.83 | 28.24 |
| 17.13 | 5.18 | 47.51 |

TABLE 3-continued

| XRPD pattern details of the crystal form C of the compound of formula (1) | | |
|---|---|---|
| Position [2θ (°)] | D spacing [Å] | Relative intensity [%] |
| 18.39 | 4.82 | 21.94 |
| 20.08 | 4.42 | 52.03 |
| 20.98 | 4.23 | 46.41 |
| 21.74 | 4.09 | 70.10 |
| 22.72 | 3.91 | 16.41 |
| 23.22 | 3.83 | 30.03 |
| 24.13 | 3.69 | 24.24 |
| 25.27 | 3.52 | 8.23 |
| 25.57 | 3.48 | 12.66 |
| 26.55 | 3.36 | 12.88 |
| 29.08 | 3.07 | 5.05 |
| 31.19 | 2.87 | 11.46 |

Embodiment 6: Preparation of the Crystal Form D of the Compound of Formula (1)

Method: 15 mg of the compound of formula (1) was weighted, and 0.05 mL of N-methyl-2-pyrrolidone and 0.45 mL of water were added, then the resulting turbid solution was stirred at 50° C. for 3 days, and centrifuged to collect the solid, and the solid was forced-air dried at 50° C. for 4 h.

Figure 10:
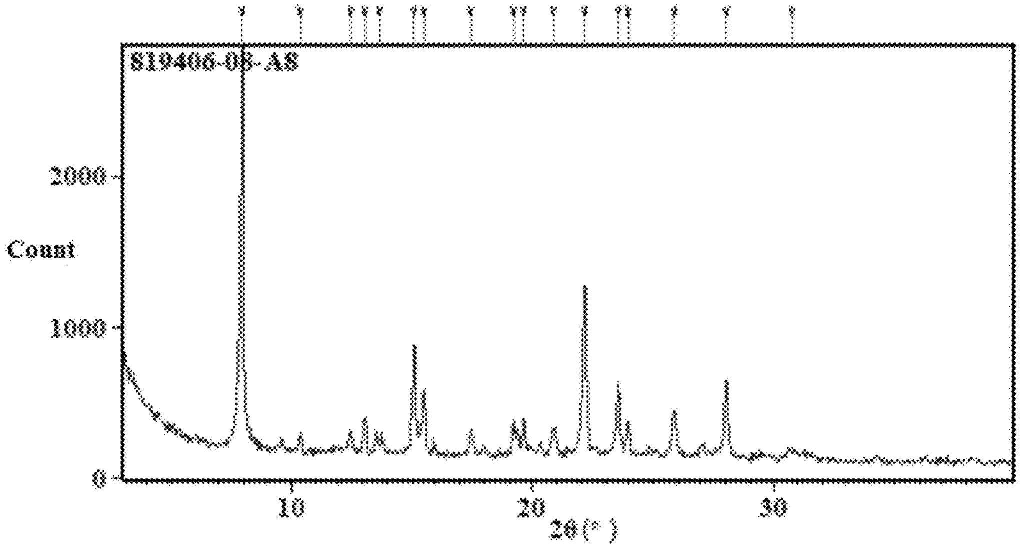
FIG. 10 is an XRPD pattern of the crystal form D of the compound of formula (1) prepared in Embodiment 6.

XRPD test was performed on the solid obtained in the above-mentioned method, and the pattern is shown in FIG. 10, there are characteristic peaks at diffraction angles 2θ=7.94, 15.09, 15.50, 19.63, 22.16, 23.56, 25.86, and 28.03 degrees, and the 2θ error range is ±0.2 degrees. Its x-ray powder diffraction data are shown in Table 4.

Figure 11:
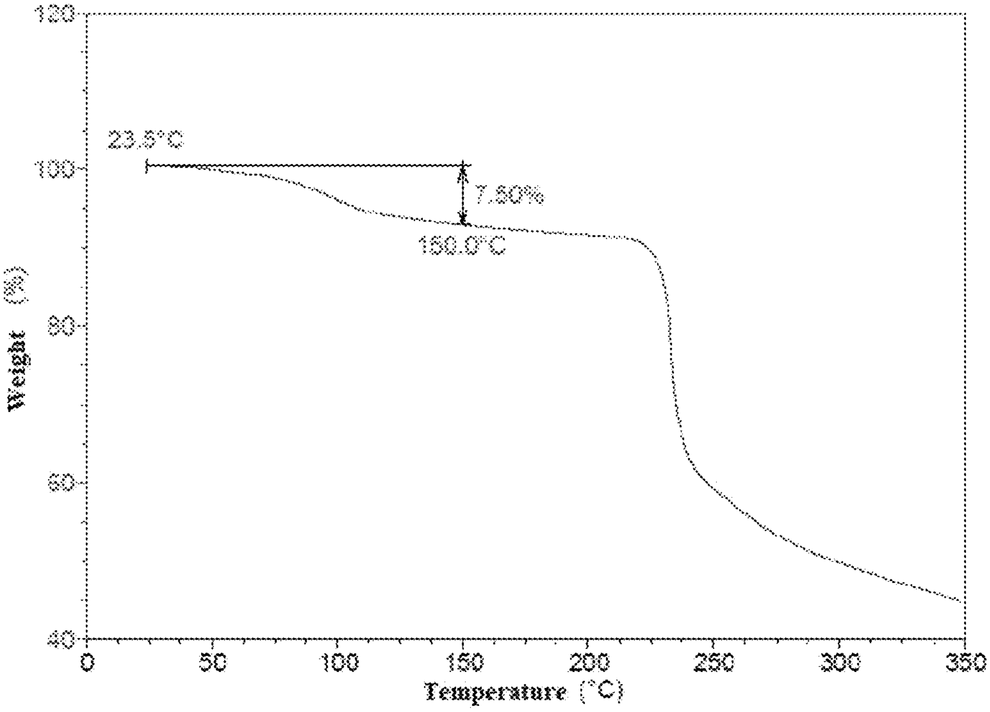
FIG. 11 is a TGA spectrum of the crystal form D of the compound of formula (1) prepared in Embodiment 6.
Figure 12:
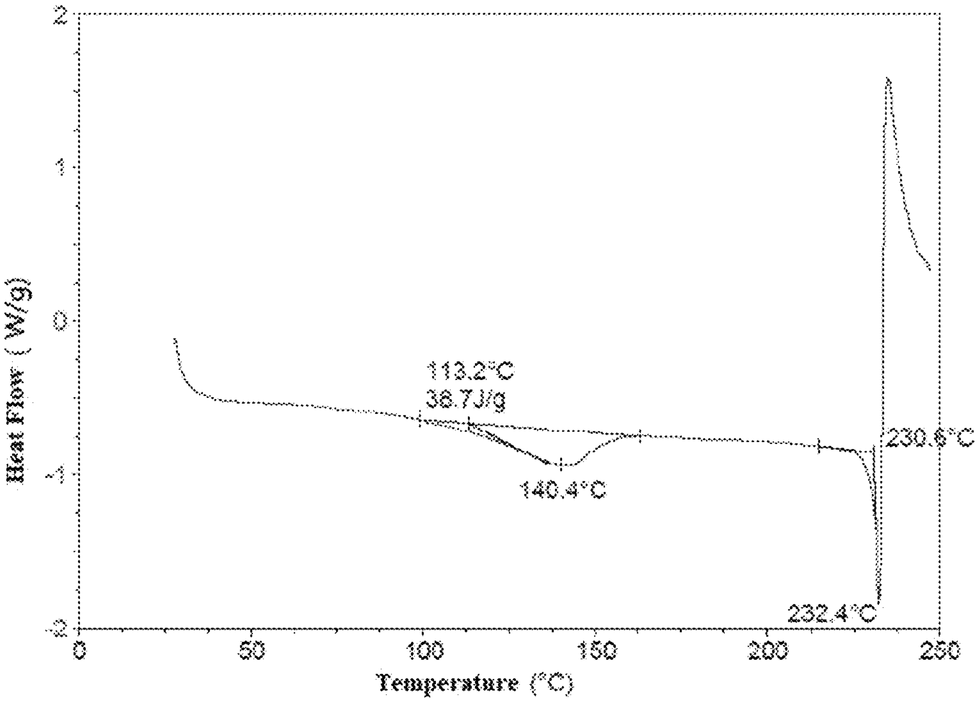
FIG. 12 is a DSC spectrum of the crystal form D of the compound of formula (1) prepared in Embodiment 6.

The results of TGA (FIG. 11) and DSC (FIG. 12) show that the sample has a weight loss of 7.5% when heated to 150° C., and has two endothermic peaks at 140.4° C. and 232.4° C. (peak values), and the crystal form D of the compound of formula (1) is an N-methyl-2-pyrrolidone solvate.

TABLE 4

| XRPD pattern details of the crystal form D of the compound of formula (1) | | |
|---|---|---|
| Position [2θ (°)] | D spacing [Å] | Relative intensity [%] |
| 7.94 | 11.13 | 100.00 |
| 10.37 | 8.53 | 3.59 |
| 12.44 | 7.11 | 5.58 |
| 13.06 | 6.78 | 9.84 |
| 13.63 | 6.50 | 2.97 |
| 15.09 | 5.87 | 29.92 |
| 15.50 | 5.72 | 17.90 |
| 17.45 | 5.08 | 7.18 |
| 19.23 | 4.62 | 9.53 |
| 19.63 | 4.52 | 10.37 |
| 20.88 | 4.25 | 7.33 |
| 22.16 | 4.01 | 46.64 |
| 23.56 | 3.78 | 19.29 |
| 23.96 | 3.71 | 9.93 |
| 25.86 | 3.45 | 13.02 |
| 28.03 | 3.18 | 21.48 |
| 30.75 | 2.91 | 2.46 |

Embodiment 7: Preparation of the Crystal Form E of the Compound of Formula (1)

Method: 15 mg of the compound of formula (1) was weighted, and 0.5 mL of N,N-dimethylacetamide was added to dissolve it, the bottle containing the resulting solution was placed in a 20 mL bottle with 4 mL of water, then the 20 mL bottle was sealed and stood at room temperature for 7 days, to give 14.3 mg while solid, with a yield of 95.2% and an HPLC purity of 99.2%.

Figure 13:
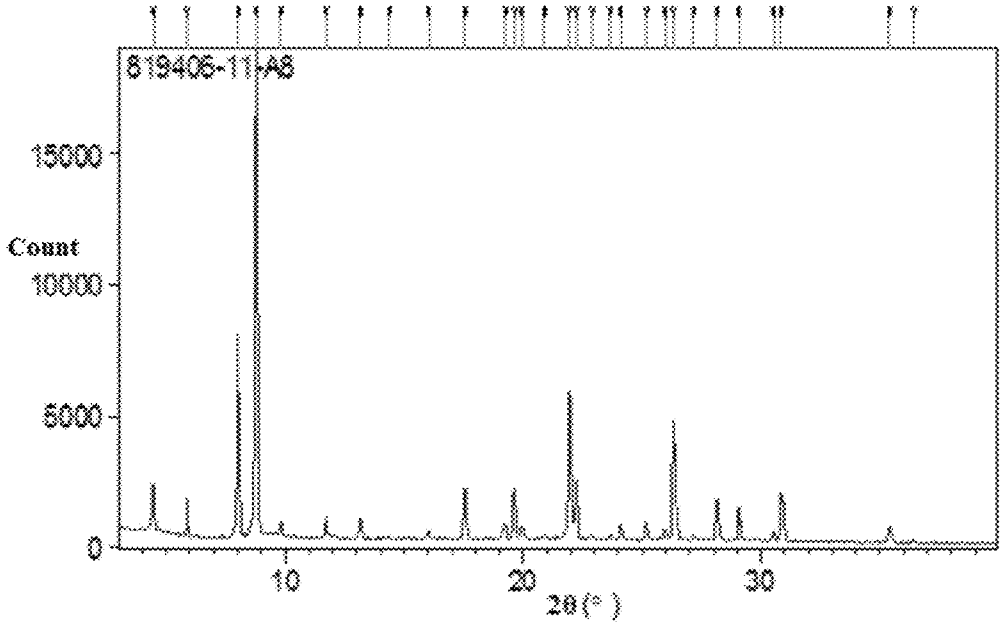
FIG. 13 is an XRPD pattern of the crystal form E of the compound of formula (1) prepared in Embodiment 7.

XRPD test was performed on the solid obtained in the above-mentioned method, and the pattern is shown in FIG. 13, there are characteristic peaks at diffraction angles 2θ=4.44, 5.87, 8.01, 8.78, 17.56, 19.64, 21.95, 22.25, 26.33, 28.15, 29.07 and 30.86 degrees, and the 2θ error range is ±0.2 degrees. Its x-ray powder diffraction data are shown in Table 5.

TABLE 5

| XRPD pattern details of the crystal form E of the compound of formula (1) | | |
|---|---|---|
| Position [2θ (°)] | D spacing [Å] | Relative intensity [%] |
| 4.44 | 19.90 | 9.67 |
| 5.87 | 15.06 | 7.32 |
| 8.01 | 11.03 | 40.52 |
| 8.78 | 10.08 | 100.00 |
| 17.56 | 5.05 | 10.44 |
| 19.64 | 4.52 | 10.13 |
| 21.95 | 4.05 | 30.07 |
| 22.25 | 4.00 | 10.80 |
| 26.33 | 3.39 | 20.19 |
| 28.15 | 3.17 | 8.35 |
| 29.07 | 3.07 | 7.12 |
| 30.86 | 2.90 | 9.45 |

Embodiment 8: Preparation of the Crystal Form F of the Compound of Formula (1)

Method 1: 33 g of the compound of formula (1) was weighted, and 40 mL of methanol was added, then the solution was stirred at 0-10° C. for 3 h, and filtered. The solid was forced-air dried at 50° C. for 8 h, to give 31.88 g white solid, with a yield of 96.6% and an HPLC purity of 99.4%.

Method 2: 33 g of the compound of formula (1) was weighted, and 40 mL of ethanol was added, then the solution was stirred at 0-10° C. for 3 h, and filtered. The solid was forced-air dried at 50° C. for 8 h, to give 30.76 g white solid, with a yield of 93.2% and an HPLC purity of 99.5%.

Method 3: 33 g of the compound of formula (1) was weighted, and 40 mL of ethyl acetate was added, then the solution was stirred at 0-10° C. for 3 h, and filtered. The solid was forced-air dried at 50° C. for 8 h, to give 31.24 g white solid, with a yield of 94.7% and an HPLC purity of 99.5%.

Figure 14:
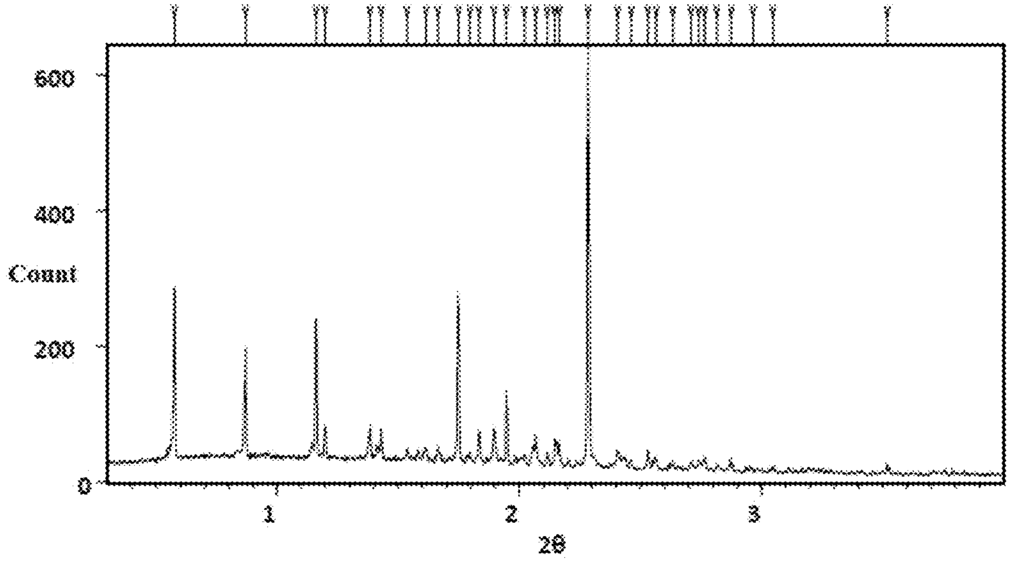
FIG. 14 is an XRPD pattern of the crystal form F of the compound of formula (1) prepared in Embodiment 8.

XRPD test was performed on the solid obtained in Method 1, and the pattern is shown in FIG. 14, there are characteristic peaks at diffraction angles 2θ=5.77, 8.69, 11.61, 11.98, 13.84, 14.30, 17.48, 18.33, 18.95, 19.47 and 22.84 degrees, and the 2θ error range is ±0.2 degrees. Its x-ray powder diffraction data are shown in Table 6.

Figure 15:
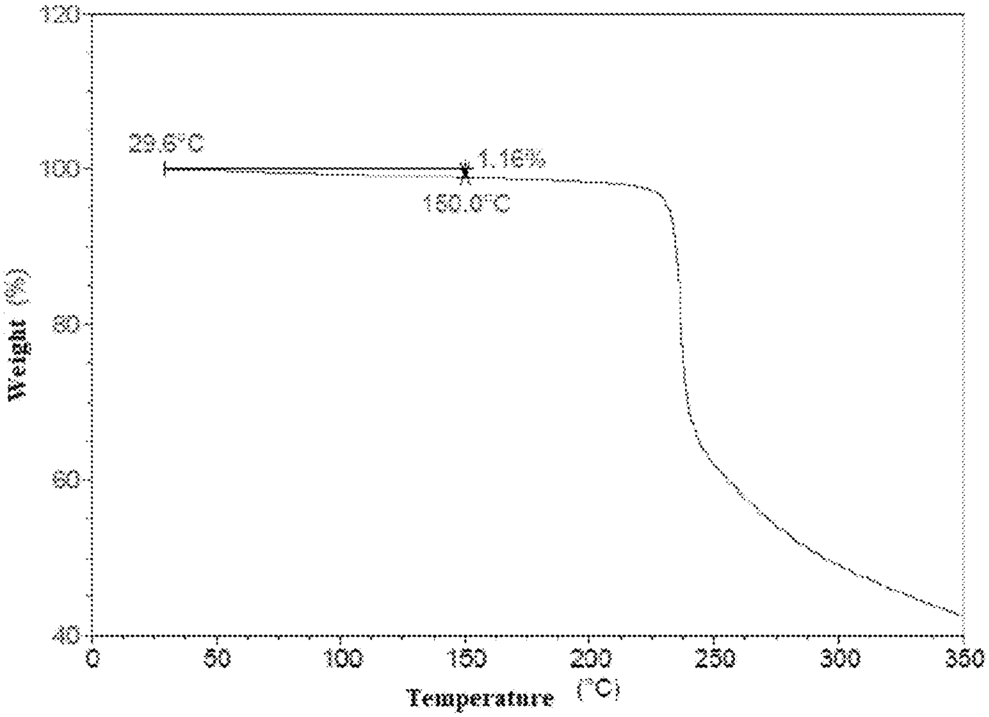
FIG. 15 is a TGA spectrum of the crystal form F of the compound of formula (1) prepared in Embodiment 8.
Figure 16:
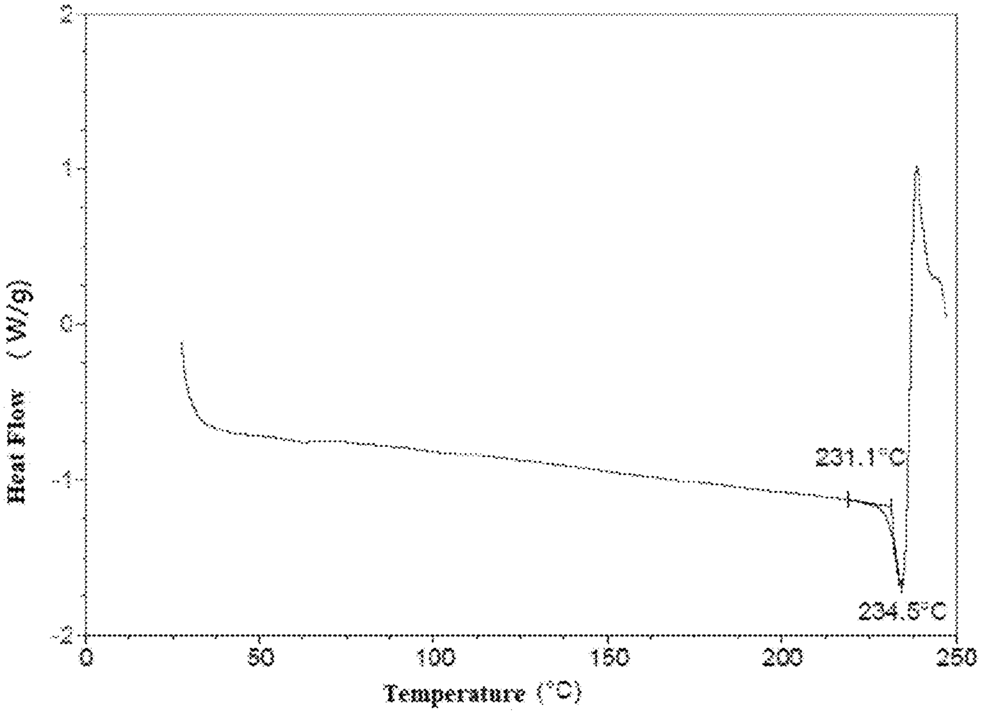
FIG. 16 is a DSC spectrum of the crystal form F of the compound of formula (1) prepared in Embodiment 8.

The results of TGA (FIG. 15) and DSC (FIG. 16) show that the sample has a weight loss of 1.2% when heated to 150° C., and has an endothermic peak at 234.5° C. (peak value), and the crystal form F of the compound of formula (1) is anhydrous crystal form.

TABLE 6

XRPD pattern details of the crystal form F of the compound of formula (1)

| Position [2θ (°)] | D spacing [Å] | Relative intensity [%] |
|---|---|---|
| 5.77 | 15.32 | 41.05 |
| 8.69 | 10.18 | 26.61 |
| 11.61 | 7.62 | 33.54 |
| 11.98 | 7.39 | 8.38 |
| 13.84 | 6.40 | 8.10 |
| 14.30 | 6.19 | 8.45 |
| 15.37 | 5.76 | 3.55 |
| 16.14 | 5.49 | 4.14 |
| 16.64 | 5.33 | 4.41 |
| 17.48 | 5.07 | 35.95 |
| 18.33 | 4.84 | 7.10 |
| 18.95 | 4.68 | 8.63 |
| 19.47 | 4.56 | 17.70 |
| 20.22 | 4.39 | 2.89 |
| 20.69 | 4.29 | 5.94 |
| 21.16 | 4.20 | 3.49 |
| 21.47 | 4.14 | 6.97 |
| 21.64 | 4.11 | 5.41 |
| 22.84 | 3.89 | 100.00 |
| 24.06 | 3.70 | 4.29 |
| 25.31 | 3.52 | 4.35 |

XRPD tests were performed on the solids obtained by other methods, and the test patterns were substantially the same as depicted in FIG. 14, indicating that the obtained solids were the crystal form F of the compound of formula (1).

The single crystal of the crystal form F of the compound of formula (1) may be prepared by the following method: dissolving the compound of formula (1) in methanol, filtering, volatilizing methanol in the filtrate at room temperature to precipitate crystals, collecting the resulting crystals by filtration, and airing at room temperature to obtain it.

Figure 17:
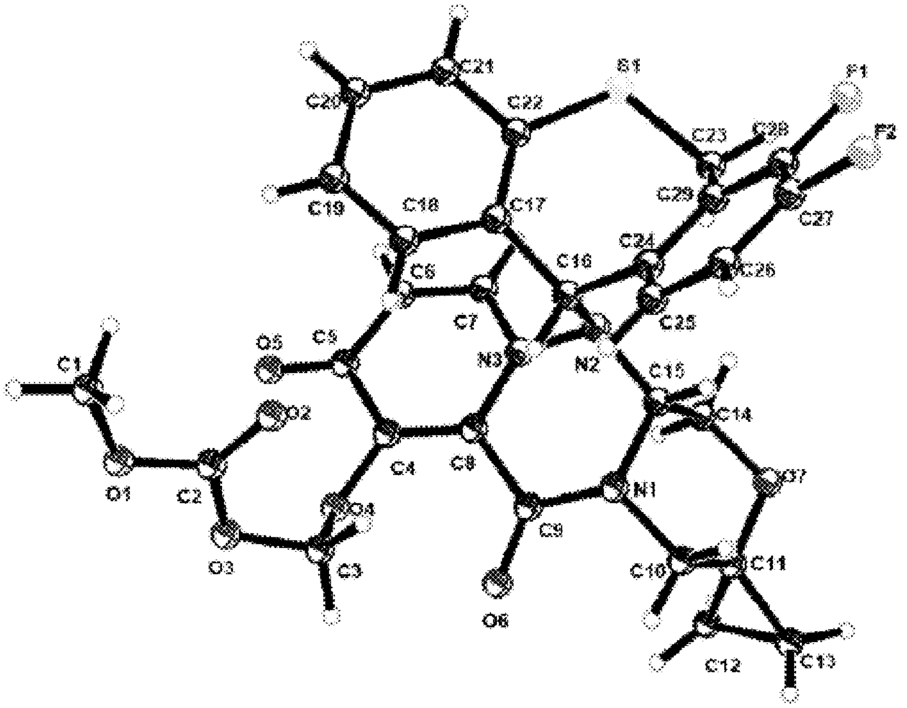
FIG. 17 is an X-ray single crystal diffraction pattern of the mono crystal of the crystal form F of the compound of formula (1) prepared in Embodiment 8.

The obtained single crystal was subjected to single crystal X-ray diffraction data collection and the single crystal structure was analyzed. See Table 7 for the single crystal structure data of the compound of formula (1). The single crystal structure analysis determined the absolute configuration of the chiral center of the compound of formula (1). As shown in FIG. 17, according to Cahn-Ingold-Prelog's R and S sequence rules, the chirality of $C_{15}$ is R and the chirality of $C_{16}$ is S.

TABLE 7 single crystal structure data of the crystal form F of the compound of formula (1)

| | |
|---|---|
| Empirical formula | $C_{29}H_{25}F_2N_3O_7S$ |
| Formula weight | 597.58 |
| Temperature | 100K |
| Wavelength | Mo Kα radiation, λ = 0.71073 Å |
| Crystal system, space group | orthorhombic crystal system, $P2_12_12_1$ |
| Unit cell dimensions | a = 11.7243 (3) Å,<br>b = 19.5693 (6) Å,<br>c = 23.3801 (7) Å,<br>α = β = γ = 90° |
| Volume | 5364.2 (3) $Å^3$ |
| Z, Calculated density | 8, 1.480 $g/cm^3$ |
| Absorption coefficient | 0.189 $mm^{-1}$ |
| F(000) | 2480 |
| Crystal size | 0.19 × 0.12 × 0.08 mm |

Embodiment 9: Evaluation of the Solid State Stability of the Crystal Form

The crystal form F samples of the compound of formula (1) were placed at 60° C. for 30 days, at 25° C./92.5% RH for 30 days, and exposed to light for 15 days, respectively. The physical and chemical stability of the samples were tested by XRPD and HPLC. The results show that under the various stability test conditions, the crystal form F samples of the compound of formula (1) have not undergone crystal form transformation and HPLC purity reduction, indicating that it has good physical and chemical stability under the test conditions (Table 8).

TABLE 8

Solid state stability of the crystal form F of the compound of formula (1)

| Conditions | Purity (area %) | Purity/ initial (%) | Crystal form change | Appearance and character |
|---|---|---|---|---|
| Initial | 98.6 | — | No | White powder |
| 60° C./ 30 days | 98.7 | 100.1 | No | White powder |
| 25° C./ 92.5% RH/ 30 days | 99.0 | 100.4 | No | White powder |
| Light*/ 15 days | 98.5 | 99.9 | No | White powder |

*White light: 4500 Lux, ultraviolet light: 90 $\mu w/cm^2$

Embodiment 10: Evaluation of Hygroscopicity of the Crystal Forms

Figure 18:
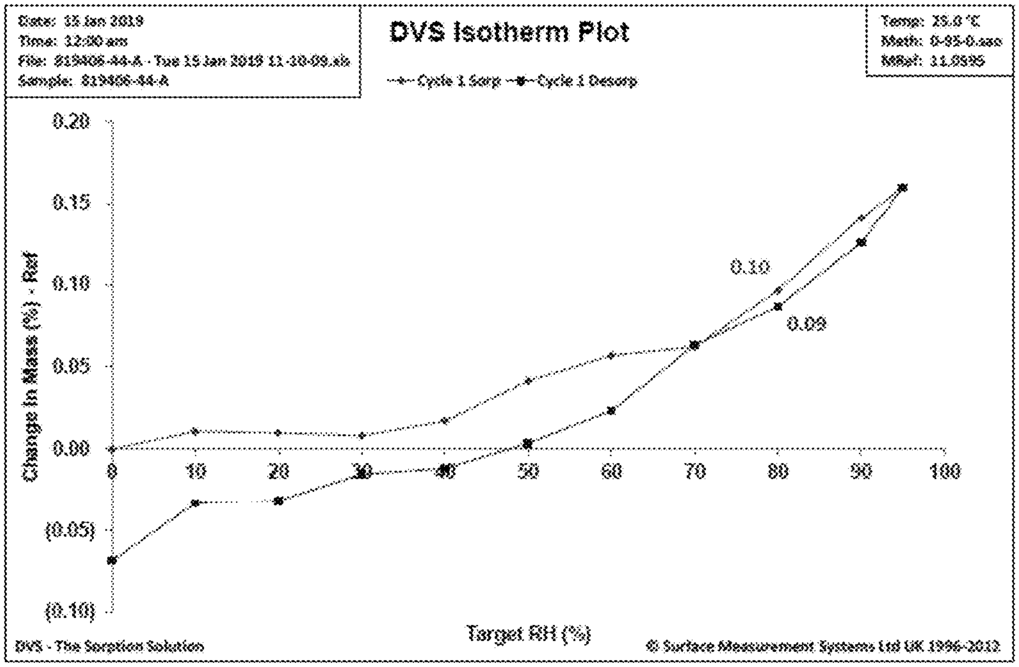
FIG. 18 is a dynamic vapour sorption spectrum of the crystal form F of the compound of formula (1) prepared in Embodiment 10.

The hygroscopicity of the crystal form F sample of the compound of formula (1) was tested by dynamic vapour sorption (DVS) test at 25° C., and the result showed that the moisture-absorption weight gain of the sample under the condition of 25° C./80% RH was 0.10% (FIG. 18), indicating that the sample has almost no hygroscopicity. At the same time, the XRPD results showed that the crystal form F of the compound of formula (1) did not change before and after the DVS test.

The stability and hygroscopicity of other crystal forms have also been studied, and the results show that they all meet the requirements for medicinal use, wherein, the crystal form F of the compound of formula (1) is the most stable and has the best hygroscopicity.

Embodiment 11: Large-Scale Production of the Crystal Form F of the Compound of Formula (1)

Figure 19:
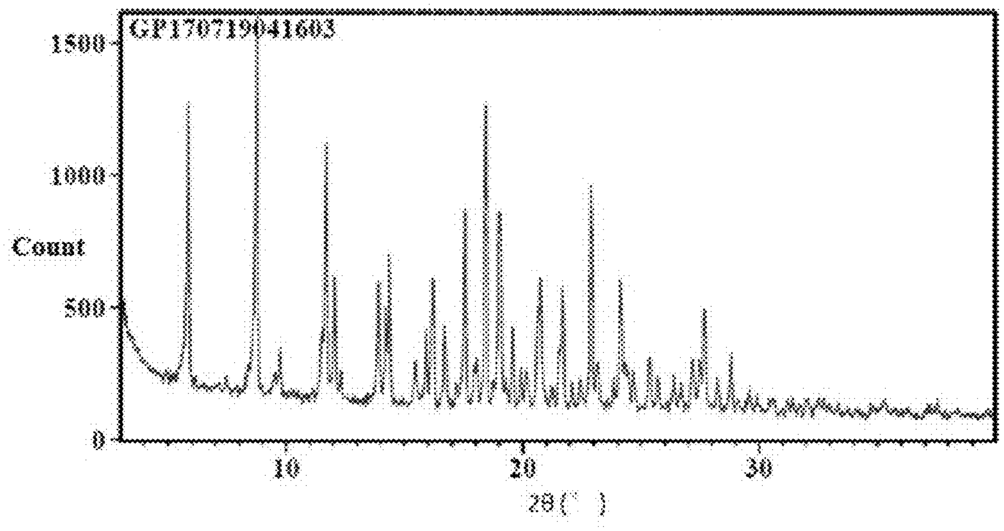
FIG. 19 is an XRPD pattern of the crystal form F of the compound of formula (1) prepared in Embodiment 11.

243.31 g of the compound of formula (2), 89.90 g of chloromethyl dimethyl carbonate, 133.20 g of potassium carbonate and 79.19 g of potassium iodide were added to 1215 mL of N,N-dimethylacetamide in a 2 L three-neck flask, and the system was heated to 45 to 55° C. to react for 5 h. HPLC monitored the reaction being complete. The system was filtered while hot, the solid was rinsed with 1215 mL of N,N-dimethylacetamide, the filtrate was merged, cooled and maintained at 0 to 10° C. Then 240 mL of 1N hydrochloric acid solution was added to adjust the pH to 1 to 2, then 4860 mL of water was added dropwise, and the system was stirred for 0.5 h and then filtered, the filter cake was rinsed with 1 L of water and suction filtered to dryness to give a crude product of the compound of formula (1). The crude product was dissolved in 3600 mL of dichloromethane, the aqueous layer was separated, the aqueous layer was extracted with 480 mL of dichloromethane, the organic layers were merged, washed with 1200 mL of water, vacuum concentrated to dryness at 40 to 50° C., and 1215 mL of acetone and 500 mL of methanol were added, then the system was heated to 50 to 60° C. to reflux, 480 mL of acetone was added to dissolve it, the system was vacuum concentrated to dryness at 40 to 50° C., and 730 mL of methanol was added, the system was heated to 50 to 60° C. and stirred for 1 h, then cooled to 0 to 10° C. to crystallize for 1 h, filtered, and the filter cake was rinses with 310 mL of cold methanol, and forced-air dried at 50° C. for 8 h to give 237.18 g of the compound of formula (1). It is the crystal form F determined by XRPD, and the pattern is shown in FIG. 19, there are characteristic peaks at diffraction angles 2θ=5.77±0.2, 8.69±0.2, 11.61±0.2, 11.98±0.2, 13.84±0.2, 14.30±0.2, 17.48±0.2, 18.33±0.2, 18.95±0.2, 19.47±0.2, and 22.84±0.2 degrees, indicating that the prepared compound of formula (1) is in the crystal form F. The relative intensities of the diffraction peaks are shown in Table 9.

TABLE 9

| XRPD pattern details of the crystal form F obtain in the large-scale production | | |
|---|---|---|
| Position [2θ (°)] | D spacing [Å] | Relative intensity [%] |
| 5.83 | 15.16 | 60.14 |
| 8.75 | 10.11 | 100.00 |
| 11.70 | 7.57 | 68.81 |
| 12.03 | 7.36 | 27.35 |
| 13.88 | 6.38 | 29.27 |
| 14.31 | 6.19 | 22.08 |
| 15.45 | 5.74 | 11.60 |
| 16.20 | 5.47 | 34.26 |
| 16.71 | 5.31 | 19.89 |
| 17.54 | 5.06 | 44.66 |
| 18.00 | 4.93 | 10.00 |
| 18.43 | 4.81 | 81.67 |
| 19.03 | 4.66 | 50.91 |
| 19.56 | 4.54 | 18.75 |
| 20.74 | 4.28 | 34.86 |
| 21.70 | 4.10 | 29.17 |
| 22.89 | 3.88 | 59.88 |
| 23.18 | 3.84 | 11.84 |
| 24.14 | 3.69 | 33.36 |
| 25.38 | 3.51 | 12.78 |
| 27.69 | 3.22 | 25.96 |
| 28.81 | 3.10 | 14.44 |

Figure 20:
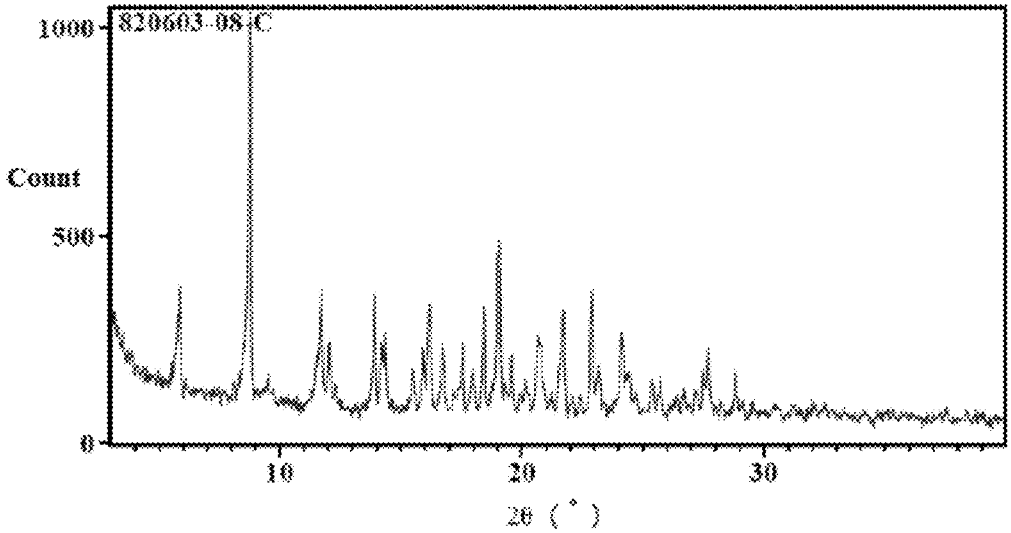
FIG. 20 is an XRPD pattern of the crystal form F of the compound of formula (1) prepared in Embodiment 11 after jet milling.

In addition, 224.90 g of the above compound of the formula (1) was jet milled (feed pressure 0.4 to 0.5 MPa, milling pressure 0.18 to 0.22 MPa) to give 212.00 g sample with a particle size of D90≤10 μm. The milled sample was tested by XRPD, as shown in FIG. 20, and the X-ray diffraction data is shown in Table 10. The results show that the crystal form does not change before and after milling, indicating that the milling process will not affect the crystal form F, and the crystal form F has good mechanical stability.

TABLE 10

| XRPD pattern details after milling | | |
|---|---|---|
| Position [2θ (°)] | D spacing [Å] | Relative intensity [%] |
| 5.84 | 15.14 | 25.37 |
| 8.75 | 10.11 | 100.00 |
| 11.70 | 7.56 | 30.63 |
| 12.03 | 7.36 | 14.15 |
| 13.90 | 6.37 | 30.36 |
| 14.28 | 6.20 | 13.17 |
| 15.47 | 5.73 | 9.20 |
| 15.92 | 5.57 | 16.53 |
| 16.19 | 5.48 | 27.80 |
| 16.73 | 5.30 | 16.21 |
| 17.52 | 5.06 | 14.00 |
| 17.94 | 4.94 | 9.48 |
| 18.43 | 4.81 | 27.35 |
| 19.04 | 4.66 | 40.97 |
| 19.55 | 4.54 | 12.76 |
| 20.67 | 4.30 | 19.44 |
| 21.70 | 4.09 | 26.34 |
| 22.89 | 3.89 | 31.87 |
| 23.19 | 3.84 | 12.56 |
| 24.13 | 3.69 | 20.40 |
| 25.39 | 3.51 | 8.15 |
| 25.73 | 3.46 | 9.24 |
| 27.70 | 3.22 | 15.63 |
| 28.80 | 3.10 | 11.19 |

The explanation on the above embodiments is only to help understanding of the method and its core concept of the present application. It should be noted that, for those ordinary skilled in the art, various improvements and modifications can be made without depart from the technical principle of the present application, and these improvements and modifications should be covered by the protective scope of the present application.

What is claimed is:

1. A crystal of a compound for Formula (1) or a solvate thereof:

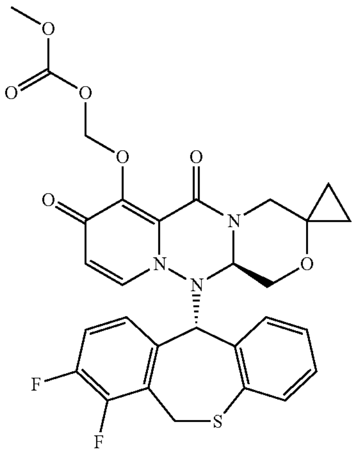

(1)

wherein, the crystal has an X-ray powder diffraction pattern with characteristic peaks at 2θ of 3.10°±0.2°, 8.74°±0.2°, 15.44°±0.2° and 21.91°±0.2°; or the crystal has an X-ray powder diffraction pattern with characteristic peaks at 2θ of 8.42°±0.2°, 14.27°±0.2°, 16.04°±0.2° and 25.41°±0.2°; or the crystal has an X-ray powder diffraction pattern with characteristic peaks at 2θ of 7.73°±0.2°, 17.13°±0.2°, 20.08°±0.2° and 21.74°±0.2°; or the crystal has an X-ray powder diffraction pattern with characteristic peaks at 2θ of 7.94°±0.2°, 22.16°±0.2° and 28.03°±0.2°; or the crystal has an X-ray powder diffraction pattern with characteristic peaks at 2θ of 8.01°±0.2°, 8.78°±0.2° and 26.33°±0.2°; or the crystal has an X-ray powder diffraction pattern with characteristic peaks at 2θ of 5.77°±0.2°, 8.69°±0.2°, 17.48°±0.2° and 22.84°±0.2°; or the crystal is in a single crystal form, which belongs to orthorhombic crystal system, with space group $P2_12_12_1$, and unit-cell parameters are: a=11.7±0.2 Å, b=19.6±0.2 Å, c=23.4±0.2 Å, α=90°±0.2°, β=90°±0.2° and γ=90°±0.2°.

2. The crystal as claimed in claim 1, wherein, the X-ray powder diffraction pattern of the crystal having characteristic peaks at 2θ 3.10°±0.2, 8.74°±0.2°, 15.44°±0.2° and 21.91°±0.2° further has one or more characteristic peaks at 2θ of 13.08°±0.2°, 26.35°±0.2°, and 30.83°±0.2°; and/or a spectrum of the crystal, determined by thermogravimetric analysis, having characteristic peaks at 2θ of 3.10°±0.2°, 8.74°±0.2°, 15.44°±0.2° and 21.91°±0.2°, shows that it loses 1.8±0.2% in weight when heated to 150±2° C.; and/or a spectrum of the crystal, determined by differential scanning calorimetry, having characteristic peaks at 2θ of 3.10°±0.2°, 8.74°±0.2°, 15.44°±0.2° and 21.91°±0.2°, shows one endothermic peak, indicating that a melting point onset temperature of the crystal is 230.5±2° C.; and/or the crystal having characteristic peaks at 2θ of 3.10°±0.2°, 8.74°±0.2°, 15.44°±0.2° and 21.91°±0.2° is an anhydrous crystal form.

3. The crystal as claimed in claim 1, wherein, the X-ray powder diffraction pattern of the crystal having characteristic peaks at 2θ of 8.42°±0.2°, 14.27°±0.2°, 16.04°±0.2° and 25.41°±0.2° further has one or two characteristic peaks at 2θ of 10.75°±0.2° and 16.87°±0.2°.

4. The crystal as claimed in claim 1, wherein, the X-ray powder diffraction pattern of the crystal having characteristic peaks at 2θ of 8.42°±0.2°, 14.27°±0.2°, 16.04°±0.2° and 25.41°±0.2° further has one or more characteristic peaks at 2θ of 18.21°±0.2°, 18.78°±0.2°, 19.26°±0.2°, 19.60°±0.2°, 20.40°±0.2°, 21.39°±0.2°, 21.66°±0.2°, 23.38°±0.2°, 27.32°±0.2°, 29.17°±0.2°, and 34.08°±0.2°; and/or a spectrum of the crystal, determined by thermogravimetric analysis, having characteristic peaks at 2θ of 8.42°±0.2°, 14.27°±0.2°, 16.04°±0.2° and 25.41°±0.2°, shows that it loses 2.2±0.2% in weight when heated to 150±2° C.; and/or;

a spectrum of the crystal, determined by differential scanning calorimetry, having characteristic peaks at 2θ of 8.42°±0.2°, 14.27°±0.2°, 16.04°±0.2° and 25.41°±0.2°, shows two endothermic peaks, and onset temperatures of the two endothermic peaks are 208.5±2° C. and 233.8±2° C., respectively; and/or the crystal having characteristic peaks at 2θ of 8.42°±0.2°, 14.27°±0.2°, 16.04°±0.2° and 25.41°±0.2° is an anhydrous crystal form.

5. The crystal as claimed in claim 1, wherein, the X-ray powder diffraction pattern of the crystal having characteristic peaks at 2θ of 7.73°±0.2°, 17.13°±0.2°, 20.08°±0.2° and 21.74°±0.2° further has one or more characteristic peaks at 2θ of 13.13°±0.2°, 13.65°±0.2°, 20.98°±0.2°, and 23.22°±0.2°.

6. The crystal as claimed in claim 1, wherein, the X-ray powder diffraction pattern of the crystal having characteristic peaks at 2θ of 7.73°±0.2°, 17.13°±0.2°, 20.08°±0.2° and 21.74°±0.2° further has one or more characteristic peaks at 2θ of 12.51°±0.2°, 14.76°±0.2°, 15.21°±0.2°, 18.39°±0.2°, and 24.13°±0.2°; and/or a spectrum of the crystal, determined by thermogravimetric analysis, having characteristic peaks at 2θ of 7.73°±0.2°, 17.13°±0.2°, 20.08°±0.2° and 21.74°±0.2°, shows that it loses 12.05±0.2% in weight when heated to 150±2° C.; and/or a spectrum of the crystal, determined by differential scanning calorimetry, having characteristic peaks at 2θ of 7.73°±0.2°, 17.13°±0.2°, 20.08°±0.2° and 21.74°±0.2°, shows two endothermic peaks, and onset temperatures of the two endothermic peaks are 86.8±2° C. and 233.9±2° C., respectively; and/or the crystal having characteristic peaks at 2θ of 7.73°±0.2°, 17.13°±0.2°, 20.08°±0.2° and 21.74°±0.2° is a tetrahydrofuran solvate of the compound of formula (1).

7. The crystal as claimed in claim 1, wherein, the X-ray powder diffraction pattern of the crystal having characteristic peaks at 2θ of 7.94°±0.2°, 22.16°±0.2°, and 28.03°±0.2° further has one or more characteristic peaks at 2θ of 15.09°±0.2°, 15.50°±0.2°, 19.63°±0.2°, 23.56°±0.2°, and 25.86°±0.2°; and/or a spectrum of the crystal, determined by thermogravimetric analysis, having characteristic peaks at 2θ of 7.94°±0.2°, 22.16°±0.2°, and 28.03°±0.2°, shows that it loses 7.5±0.2% in weight when heated to 150±2° C.; and/or a spectrum of the crystal, determined by differential scanning calorimetry, having characteristic peaks at 2θ of 7.94°±0.2°, 22.16°±0.2°, and 28.03°±0.2°, shows two endothermic peaks, and onset temperatures of the two endothermic peaks are 113.2±2° C. and 230.6±2° C., respectively; and/or the crystal having characteristic peaks at 2θ of 7.94°±0.2°, 22.16°±0.2°, and 28.03°±0.2° is a N-methyl-2-pyrrolidone solvate of the compound of formula (1).

8. The crystal as claimed in claim 1, wherein, the X-ray powder diffraction pattern of the crystal having characteristic peaks at 2θ of 8.01°±0.2°, 8.78°±0.2°, and 26.33°±0.2° further has one or more characteristic peaks at 2θ of 4.44°±0.2°, 17.56°±0.2°, 21.95°±0.2, and 22.25°±0.2°.

9. The crystal as claimed in claim 1, wherein, the X-ray powder diffraction pattern of the crystal having characteristic peaks at 2θ of 8.01°±0.2°, 8.78°±0.2°, and 26.33°±0.2° further has one or more characteristic peaks at 2θ of 5.87°±0.2°, 19.64°±0.2°, 28.15°±0.2°, 29.07°±0.2°, and 30.86°±0.2°.

10. The crystal as claimed in claim 1, wherein, the X-ray powder diffraction pattern of the crystal having characteristic peaks at 2θ of 5.77°±0.2°, 8.69°±0.2°, 17.48°±0.2° and 22.84°±0.2° further has one or two characteristic peaks at 2θ of 11.61°±0.2° and 19.47°±0.2°.

11. The crystal as claimed in claim 1, wherein, the X-ray powder diffraction pattern of the crystal having characteristic peaks at 2θ of 5.77°±0.2°, 8.69°±0.2°, 17.48°±0.2° and 22.84°±0.2° further has one or more characteristic peaks at 2θ of 11.98°±0.2°, 13.84°±0.2°, 14.30°±0.2°, 18.33°±0.2°, and 18.95°±0.2°; and/or a spectrum of the crystal, determined by differential scanning calorimetry having characteristic peaks at 2θ of 5.77°±0.2°, 8.69°±0.2°, 17.48°±0.2° and 22.84°±0.2°, shows an endothermic peak, and onset temperature of the endothermic peak is 231.1±2° C.; and/or the crystal having characteristic peaks at 2θ of 5.77°±0.2°, 8.69°±0.2°, 17.48°±0.2° and 22.84°±0.2° is an anhydrous crystal form.

12. The crystal as claimed in claim 1, wherein, the unit-cell parameters are: a=11.65-11.75 Å, b=19.50-19.60 Å, c=23.33-23.43 Å, α=89.9-90.1°, β=89.9-90.1°, ±=89.9-90.1°.

13. The crystal as claimed in claim 1, wherein, the X-ray powder diffraction pattern of the crystal has characteristic peaks at 2θ of 3.10°±0.2°, 8.74°±0.2°, 13.08°±0.2°, 15.44°±0.2°, 21.91°±0.2°, 26.35°±0.2°, and 30.83°±0.2°; or the X-ray powder diffraction pattern of the crystal has characteristic peaks at 2θ of 8.42°±0.2°, 10.75°±0.2°, 14.27°±0.2°, 16.04°±0.2°, 16.87°±0.2°, 18.21°±0.2°, 18.78°±0.2°, 19.26°±0.2°, 19.60°±0.2°, 20.40°±0.2°, 21.39°±0.2°, 21.66°±0.2°, 23.38°±0.2°, 25.41°±0.2°, 27.32°±0.2°, 29.17°±0.2°, and 34.08°±0.2°; or the X-ray powder diffraction pattern of the crystal has characteristic peaks at 2θ of 7.73°±0.2°, 12.51°±0.2°, 13.13°±0.2°, 13.65°±0.2°, 14.76°±0.2°, 15.21°±0.2°, 17.13°±0.2°, 18.39°±0.2°, 20.08°±0.2°, 20.98°±0.2°, 21.74°±0.2°, 23.22°±0.2°, and 24.13°±0.2°; or the X-ray powder diffraction pattern of the crystal has characteristic peaks at 2θ of 7.94°±0.2°, 15.09°±0.2°, 15.50°±0.2°, 19.63°±0.2°, 22.16°±0.2°, 23.56°±0.2°, 25.86°±0.2°, and 28.03°±0.2; or the X-ray powder diffraction pattern of the crystal has characteristic peaks at 2θ of 4.44°±0.2°, 5.87°±0.2°, 8.01°±0 2° 8.78°+0.2°, 17.56°±0.2°, 19.64°±0.2°, 21.95°±0.2°, 22.25°±0.2°, 26.33°±0.2°, 28.15°±0.2°, 29.07°±0.2°, and 30.86°±0.2°; or the X-ray powder diffraction pattern of the crystal characteristic peaks at 2θ of 5.77°±0.2°, 8.69°±0.2°, 11.61°±0.2°, 11.98°±0.2°, 13.84°±0.2°, 14.30°±0.2°, 17.48°±0.2°, 18.33°±0.2°, 18.95°±0.2°, 19.47°±0.2°, and 22.84°±0.2°; or the unit-cell parameters of the single crystal form are: a=11.7243 (3) Å, b=19.5693 (6) Å, c=23.3801 (7) Å, and α=β=γ=90°.

14. The crystal as claimed in claim 1, wherein, an XRPD pattern of the crystal is the same as shown in FIG. 1, FIG. 4, FIG. 7, FIG. 10, FIG. 13, FIG. 19 or FIG. 20.

15. A preparation method for the crystal as claimed in claim 1, wherein, the preparation method comprises:

adding the compound of formula (1) to one or more of an ester solvent, an alcohol solvent, and a ketone solvent to dissolve, then mixing with a hydrocarbon solvent, crystallizing, filtering, and drying to give the crystal having characteristic peaks at 2θ of 3.10°±0.2°, 8.74°±0.2°, 15.44°±0.2° and 21.91°±0.2°; or adding the compound of formula (1) to a ketone solvent, volatilizing the solvent at room temperature to obtain a solid, and drying the resulting solid to give the crystal having characteristic peaks at 2θ of 3.10°±0.2°, 8.74°±0.2°, 15.44°±0.2° and 21.91°±0.2°; or adding the compound of formula (1) to an ether solvent, stirring at room temperature, filtering to obtain a solid, and drying the resulting solid to give the crystal having characteristic peaks at 2θ of 3.10°±0.2°, 8.74°±0.2°, 15.44°±0.2° and 21.91°±0.2°; or adding the compound of formula (1) to water, stirring at 45-55° C., filtering to obtain a solid, and drying the resulting solid to give the crystal having characteristic peaks at 2θ of 3.10°±0.2°, 8.74°±0.2°, 15.44°±0.2° and 21.91°±0.2°; or adding the compound of formula (1) to a mixture solvent of a hydrocarbon solvent and an ether solvent, stirring at a set temperature for 1 to 3 h, then heating up or cooling at a rate of 0.1±0.05° C./min to circulate the temperature of the system between the set temperature and 5° C. for several times, and finally stirring at 3-7° C., filtering to obtain a solid, and drying the resulting solid to give the crystal having characteristic peaks at 2θ of 3.10°±0.2°, 8.74°±0.2°, 15.44°±0.2° and 21.91°±0.2°, the set temperature is 45 to 55° C.; or adding the compound of formula (1) to an alcohol solvent or a ketone solvent or a mixture thereof to dissolve, mixing with water, crystallizing, filtering to obtain a solid, and drying the resulting solid to give the crystal having characteristic peaks at 2θ of 8.42°±0.2°, 14.27°±0.2°, 16.04°±0.2° and 25.41°±0.2°; or adding the compound of formula (1) to a halohydrocarbon solvent, volatilizing the solvent at room temperature to obtain a solid, and drying the resulting solid to give the crystal having characteristic peaks at 2θ of 8.42°±0.2°, 14.27°±0.2°, 16.04°±0.2° and 25.41°±0.2°; or adding the compound of formula (1) to a hydrocarbon solvent, stirring at room temperature, filtering to obtain a solid, and drying the resulting solid to give the crystal having characteristic peaks at 2θ of 8.42°±0.2°, 14.27°±0.2°, 16.04°±0.2° and 25.41°±0.2°; or adding the compound of formula (1) to 2-methyltetrahydrofuran, stirring at a first set temperature, filtering and collecting a supernatant, and cooling the supernatant from a first set temperature to a second set temperature at a rate of 0.1±0.05° C./min and maintaining at the second set temperature, collecting a precipitated solid, and drying the resulting solid to give the crystal having characteristic peaks at 2θ of 8.42°±0.2°, 14.27°±0.2°, 16.04°±0.2° and 25.41°±0.2°, the first set temperature is 45 to 55° C., and the second set temperature is 0 to 10° C.; or adding the compound of formula (1) to a mixture system of tetrahydrofuran and a hydrocarbon solvent to form a turbid solution, stirring at a first set temperature, filtering and collecting a supernatant, and cooling the supernatant from a first set temperature to a second set temperature at a rate of 0.1±0.05° C./min and maintaining at the second set temperature, collecting a precipitated solid, and drying the resulting solid to give the crystal having characteristic peaks at 2θ of 7.73°±0.2°, 17.13°±0.2°, 20.08°±0.2° and 21.74°±0.2°, the first set temperature is 45 to 55° C., and the second set temperature is 0 to 10° C.; or adding the compound of formula (1) to a mixture of N-methyl-2-pyrrolidone and water to form a turbid solution, stirring at 45-55° C., filtering to obtain a solid, and drying the resulting solid to give the crystal having characteristic peaks at 2θ of 7.94°±0.2°, 22.16°±0.2°, and 28.03°±0.2°; or dissolving the compound of formula (1) in N,N-dimethylacetamide, obtaining a solid by gas-liquid diffusion in an atmosphere of water or an alcohol solvent, and filtering to give the crystal having characteristic peaks at 2θ of 8.01°±0.2°, 8.78°±0.2°, and 26.33°±0.2°; or adding the compound of formula (1) to an ester solvent or an alcohol solvent or a mixture thereof to form a turbid solution, stirring at 0-10° C., filtering to obtain a solid, and drying the resulting solid to give the crystal having characteristic peaks at 2θ of 5.77°±0.2°, 8.69°±0.2°, 17.48°±0.2° and 22.84°±0.2°; or dissolving the compound of formula (1) in an alcohol solvent, filtering, volatilizing the solvent in a filtrate at room temperature to precipitate crystals, collecting the resulting crystals by filtration, and drying at room temperature to obtain the single crystal form.

16. The preparation method as claimed in claim 15, wherein, in the method for preparing the crystal having characteristic peaks at 2θ of 5.77°±0.2°, 8.69°±0.2°, 17.48°±0.2° and 22.84°±0.2°, the ester solvent is ethyl acetate; and/or, the alcohol solvent is methanol and/or ethanol; and/or, stirring time is 2-4 h; and/or, before stirring the turbid solution at 0-10° C., heating the turbid solution to 30-60° C., and stirring at this temperature for more than 5 min.

17. A pharmaceutical composition containing the crystal as claimed in claim 1 and a pharmaceutically acceptable carrier.

18. A method for preventing and/or treating a viral infection disease, wherein, the method comprises administering to an animal or human in need of prevention and/or treatment an effective amount of the crystal of the compound of formula (1) as claimed in claim 1.

19. The method as claimed in claim 18, wherein, the viral infection disease is an infectious disease caused by influenza A virus and/or influenza B virus.

20. A method for preventing and/or treating a viral infection disease, wherein, the method comprises administering to an animal or human in need of prevention and/or treatment an effective amount of the pharmaceutical composition as claimed in claim 17.

21. The method as claimed in claim 20, wherein, the viral infection disease is an infectious disease caused by influenza A virus and/or influenza B virus.

22. A crystal of a compound of Formula (1):

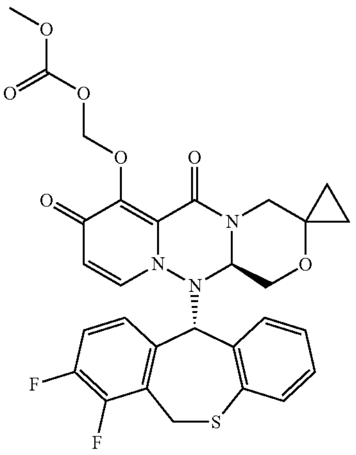

(1)

wherein, the crystal of the compound of formula (1) has an X-ray powder diffraction pattern with characteristic peaks at 2θ of 5.77°±0.2°, 8.69°±0.2°, 17.48°±0.2° and 22.84°±0.2°.

23. The crystal as claimed in claim 22, wherein, the X-ray powder diffraction pattern of the crystal of the compound of formula (1) further has one or two characteristic peaks at 2θ of 11.61°±0.2° and 19.47°±0.2°.

24. The crystal as claimed in claim 23, wherein, the X-ray powder diffraction pattern of the crystal of the compound of formula (1) further has one or more characteristic peaks at 2θ of 11.98°±0.2°, 13.84°±0.2°, 14.30°±0.2°, 18.33°±0.2°, and 18.95°±0.2°; and/or a spectrum of the crystal of the compound of formula (1) determined by differential scanning calorimetry shows an endothermic peak, and onset temperature of the endothermic peak is 231.1±2° C.; and/or the crystal of the compound of formula (1) is an anhydrous crystal form.

25. The crystal as claimed in claim 22, wherein, the X-ray powder diffraction pattern of the crystal of the compound of formula (1) further has one or more characteristic peaks at 2θ of 11.98°±0.2°, 13.84°±0.2°, 14.30°±0.2°, 18.33°±0.2°, and 18.95°±0.2°; and/or a spectrum of the crystal of the compound of formula (1) determined by differential scanning calorimetry shows an endothermic peak, and onset temperature of the endothermic peak is 231.1±2° C.; and/or the crystal of the compound of formula (1) is an anhydrous crystal form.

26. The crystal as claimed in claim 22, wherein, the X-ray powder diffraction pattern of the crystal of the compound of formula (1) has characteristic peaks at 2θ of 5.77°±0.2°, 8.69°±0.2°, 11.61°±0.2°, 11.98°±0.2°, 13.84°±0.2°, 14.30°±0.2°, 17.48°±0.2°, 18.33°±0.2°, 18.95°±0.2°, 19.47°±0.2° and 22.84°±0.2°.

27. The crystal as claimed in claim 22, wherein, an XRPD pattern of the crystal of the compound of formula (1) is the same as shown in FIG. 19.

28. A preparation method for the crystal as claimed in claim 22, wherein, the preparation method comprises:

adding the compound of formula (1) to an ester solvent or an alcohol solvent or a mixture thereof to form a turbid solution, stirring at 0-10° C., filtering to obtain a solid, and drying the resulting solid to give the crystal.

29. A pharmaceutical composition containing the crystal as claimed in claim 22 and a pharmaceutically acceptable carrier.

30. A method for preventing and/or treating a viral infection disease, wherein, the method comprises administering to an animal or human in need of prevention and/or treatment an effective amount of the pharmaceutical composition as claimed in claim 29.

31. The method as claimed in claim 30, wherein, the viral infection disease is an infectious disease caused by influenza A virus and/or influenza B virus.

32. A method for preventing and/or treating a viral infection disease, wherein, the method comprises administering to an animal or human in need of prevention and/or treatment an effective amount of the crystal of the compound of formula (1) as claimed in claim 22.

33. The method as claimed in claim 32, wherein, the viral infection disease is an infectious disease caused by influenza A virus and/or influenza B virus.

* * * * *